(12) United States Patent
Habben et al.

(10) Patent No.: US 12,410,439 B2
(45) Date of Patent: Sep. 9, 2025

(54) REDUCED STATURE MAIZE AND MADS-BOX TRANSCRIPTION FACTORS

(71) Applicant: PIONEER HI-BRED INTERNATIONAL, INC., Johnston, IA (US)

(72) Inventors: Jeffrey Habben, Urbandale, IA (US); Benjamin P Weers, Polk City, IA (US); Jingrui Wu, Johnston, IA (US)

(73) Assignee: PIONEER HI-BRED INTERNATIONAL, INC., Johnston, IA (US)

( * ) Notice: Subject to any disclaimer, the term of this patent is extended or adjusted under 35 U.S.C. 154(b) by 311 days.

(21) Appl. No.: 17/757,595

(22) PCT Filed: Dec. 15, 2020

(86) PCT No.: PCT/US2020/064999
§ 371 (c)(1),
(2) Date: Jun. 17, 2022

(87) PCT Pub. No.: WO2021/126797
PCT Pub. Date: Jun. 24, 2021

(65) Prior Publication Data
US 2022/0378000 A1   Dec. 1, 2022

Related U.S. Application Data

(60) Provisional application No. 62/949,206, filed on Dec. 17, 2019.

(51) Int. Cl.
*A01H 6/46* (2018.01)
*C12N 15/82* (2006.01)

(52) U.S. Cl.
CPC ....... *C12N 15/8262* (2013.01); *A01H 6/4684* (2018.05); *Y02A 40/146* (2018.01)

(58) Field of Classification Search
None
See application file for complete search history.

(56) References Cited

U.S. PATENT DOCUMENTS

| | | | |
|---|---|---|---|
| 6,118,055 A | 9/2000 | Livesey | |
| 7,268,272 B2 | 9/2007 | Harberd et al. | |
| 8,134,047 B2 | 3/2012 | Stonaker et al. | |
| 10,881,057 B2 | 1/2021 | Cannon et al. | |
| 11,214,842 B2 | 1/2022 | Barten et al. | |
| 11,319,550 B2 | 5/2022 | Allen et al. | |
| 11,414,670 B2 | 8/2022 | Allen et al. | |
| 11,421,242 B2 * | 8/2022 | Christensen | C12N 15/8271 |
| 11,441,153 B2 | 9/2022 | Dietrich et al. | |
| 11,472,852 B2 | 10/2022 | Alves-Junior et al. | |
| 11,627,736 B2 | 4/2023 | Barten et al. | |
| 11,632,921 B2 | 4/2023 | Cannon et al. | |
| 12,077,766 B2 | 9/2024 | La Rota et al. | |
| 2002/0120111 A1 | 8/2002 | Choe et al. | |
| 2002/0162142 A1 | 10/2002 | Johal et al. | |
| 2004/0019927 A1 | 1/2004 | Sherman et al. | |
| 2004/0045049 A1 | 3/2004 | Zhang et al. | |
| 2007/0192889 A1 | 8/2007 | La Rosa et al. | |
| 2010/0192259 A1 | 7/2010 | Spangenberg et al. | |
| 2011/0225665 A1 | 9/2011 | Tuinstra et al. | |
| 2014/0289900 A1 | 9/2014 | Poraty-Gavra et al. | |
| 2015/0059010 A1 | 2/2015 | Cigan et al. | |
| 2016/0319375 A1 | 11/2016 | Barten et al. | |
| 2017/0159067 A1 | 6/2017 | Charne et al. | |
| 2018/0305774 A1 | 10/2018 | Christianson et al. | |
| 2020/0199609 A1 | 6/2020 | Gao et al. | |
| 2020/0283806 A1 | 9/2020 | Koch et al. | |
| 2020/0377900 A1 | 12/2020 | Cargill et al. | |
| 2021/0032646 A1 | 2/2021 | Manjunath et al. | |
| 2021/0032649 A1 | 2/2021 | Manjunath et al. | |
| 2021/0032653 A1 | 2/2021 | Dietrich et al. | |
| 2021/0040498 A1 | 2/2021 | Manjunath et al. | |
| 2021/0363538 A1 | 11/2021 | Dietrich et al. | |
| 2022/0039320 A1 | 2/2022 | Barten et al. | |
| 2022/0159905 A1 | 5/2022 | Barten et al. | |
| 2022/0162713 A1 | 5/2022 | Barten et al. | |
| 2022/0195450 A1 | 6/2022 | Manjunath et al. | |
| 2022/0298527 A1 | 9/2022 | Dietrich et al. | |
| 2022/0307042 A1 | 9/2022 | Dietrich et al. | |
| 2022/0364108 A1 | 11/2022 | Allen et al. | |
| 2023/0110884 A1 | 4/2023 | Allen et al. | |
| 2023/0242931 A1 | 8/2023 | Dietrich et al. | |
| 2023/0265132 A1 | 8/2023 | Alves-Junior et al. | |
| 2023/0292733 A1 | 9/2023 | Barten et al. | |
| 2023/0323381 A1 | 10/2023 | Cannon et al. | |
| 2024/0090396 A1 | 3/2024 | Atwood et al. | |

FOREIGN PATENT DOCUMENTS

| | | | |
|---|---|---|---|
| WO | 9909174 A1 | 2/1999 | |
| WO | 0134818 A2 | 5/2001 | |
| WO | 2006113897 A2 | 10/2006 | |

(Continued)

OTHER PUBLICATIONS

Wei et al., Heredity 121.1 (2018): 75-86 (Year: 2018).*
Rhoads D.M. et al. Regulation of the cyanide-resistant alternative oxidase of plant mitochondria. Identification of the cysteine residue involved in alpha-keto acid stimulation and intersubunit disulfide bond formation. J Biol Chem. Nov. 13, 1998;273(46):30750-6. (Year: 1998).*
Wang et al. Genes controlling plant architecture. Curr. Opin. Biotechnol. Apr. 2006; 17(2):123-9. Epub Feb. 28, 2006. (Year: 2006).*
Hammad, 1935-1942; "Maize Response to Time and Rate of Nitrogen Application"; Pakistan Journal of Botany; vol. 43, No. 4, Web 2011; abstract; p. 135, first column, second paragraph; p. 135, second column, second paragraph.

(Continued)

*Primary Examiner* — Cynthia E Collins

(57) ABSTRACT

The compositions and methods relate to shorter stature corn plants having an increased and extended expression of a MADS-box polypeptide along with one or more genetic modifications that result in shorter stature.

12 Claims, 1 Drawing Sheet
Specification includes a Sequence Listing.

(56) References Cited

FOREIGN PATENT DOCUMENTS

| | | | |
|---|---|---|---|
| WO | 2007124312 A2 | 11/2007 | |
| WO | 2009000789 A1 | 12/2008 | |
| WO | 2009091518 A2 | 7/2009 | |
| WO | 2013086499 A2 | 6/2013 | |
| WO | 2014033723 A1 | 3/2014 | |
| WO | 20141650304 A1 | 10/2014 | |
| WO | 2016176286 A1 | 11/2016 | |
| WO | 2017054721 A1 | 4/2017 | |
| WO | 2018035354 A1 | 2/2018 | |
| WO | WO 2018/119225 * | 6/2018 | ............... A01H 1/04 |
| WO | 2019055141 A1 | 3/2019 | |
| WO | 2019161144 A1 | 8/2019 | |
| WO | 2019204253 A1 | 10/2019 | |
| WO | 2020168166 A2 | 8/2020 | |
| WO | 2022109286 A1 | 5/2022 | |
| WO | 2023097239 A1 | 6/2023 | |

OTHER PUBLICATIONS

Westgate, Feb. 1997; "Rapid Canopy Closure for Maize Production in the Northern US Corn Belt", Radiation—use efficiency and grain yield, 249-258, Field Crops Research, vol. 49, Web page 250, first column, first paragraph, DOI: 10.1016/S0378-4290(96)01055-6.

Woloshuk, Sep. 2014; "Fusarium Ear Rot" 1-3. Diseases of Corn. Purdue Extension. BP-86-W. Web. p. 2—, first-second paragraphs; p. 50, fifth paragraph.

International Search Report and Written Opinion for International Application No. PCT/US20/64999, Mailed May 6, 2021.

Wu J., et al., "Overexpression of zmm28 Increases Maize Grain Yield in the Field," Proceedings of the National Academy of Sciences, Nov. 19, 2019, vol. 116, No. 47, pp. 23850-23858, DOI: 10.1073/pnas. 1902593116, ISSN 0027-8424, XP055654707.

Yin X., et al., "In-Season Prediction of Corn Yield Using Plant Height under Major Production Systems," Agronomy Journal, May 2011, vol. 103, Issue 3, pp. 923-929.

Yu F., et al., "Genotyping-by-Sequencing Reveals Three QTL for Clubroot Resistance to Six Pathotypes of Plasmodiophora Brassicae in *Brassica rapa*," Scientific Reports, Jul. 3, 2017, vol. 7, No. 1, DOI: 10.1038/s41598-017-04903-2, XP055496842.

Zhang Y., et al., "OsMPH1 Regulates Plant Height and Improves Grain Yield in Rice," PLOS ONE, Jul. 14, 2017, vol. 12, No. 7(e0180825), 17 Pages, XP055583756.

Andersen J.P., et al., "Validation of Dwarf8 Polymorphisms Associated with Flowering Time in Elite European Inbred Lines of Maize (*Zea mays* L.)," Theoretical and Applied Genetics, International Journal of Plant Breeding Research, Springer, Berlin, De, Jul. 1, 2005, vol. 111, No. 2, pp. 206-217, doi: 10.1007/S00122-005-1996-6, ISSN 1432-2242, XP019321961.

Anonymous., "Canola Trait Polymorphisms and Sequences to Detect," Research Disclosure, 2015, vol. 61, No. 32, XP007144564, ISSN: 0374-4353, 12 Pages.

Bernardo R: "Genomewide Selection to Introgress Exotic Dwarf-Corn Germplasm Into U.S. Corn Belt Germplasm," Project Status Report Submitted to USDA Research, Education, and Economics information System, 2009-2013, 4 Pages.

Boliva L.M.A., "Molecular Analyses of Internode Elongation and Cold Stress Tolerance in Maize," Doctor of Philosophy Thesis, University of Guelph, Retrieved from Library and Archives Canada, 2016, 162 Pages.

Cassani E., et al., "Characterization of the First Dominant dwarf Maize Mutant Carrying a Single Amino Acid Insertion in the VHYNP Domain of the dwarf8 Gene," Molecular Breeding, 2009, vol. 24, No. 4, pp. 375-385.

Char S.N., et al., "An Agrobacterium-delivered CRISPR/Cas9 System for High-frequency Targeted Mutagenesis in Maize," Plant Biotechnology Journal, 2017, vol. 15, No. 2, pp. 257-268.

Chen J., et al., "Identification of Novel QTLs for Isolate-Specific Partial Resistance to Plasmodiophora brassicae in Brassica rapa" PLoS ONE, Dec. 10, 2013, vol. 8(12), pp. 1-12, e85307. doi:10.1371/journal.pone.0085307.

Chen Z., et al., "Development of Dwarfish and Yield-Effective GM Maize through Passivation of Bioactive Gibberellin," Transgenic Research, 2019, vol. 28, No. 5-6, pp. 589-599.

Chu M., et al., "Fine mapping of Rcr1 and analyses of its effect on transcriptome patterns during infection by Plasmodiophora brassicae" BMC Genomics, Dec. 23, 2014, vol. 15(1):1166, pp. 1-20, doi: 10.1186/1471-2164-15-1166.

Database maizeGDB [Online] Jun. 16, 2023, Variation record D8-N1591, Retrieved from maizeGDB, Maize Genetics and Genomics Database.

Extended European Search Report for European Application No. 18856566.7, mailed Jan. 24, 2022, 17 Pages.

Feng Z., et al., "Efficient Genome Editing in Plants Using a CRISPR/Cas system," Cell Research, 2013, vol. 23, No. 10, pp. 1229-1232.

Fornal S., et al., "ZmMYB31 Directly Represses Maize Lignin Genes and Redirects the Phenylpropanoid Metabolic Flux : ZmMYB31 Controls Phenylpropanoids," The Plant Journal, GB, Oct. 8, 2010, vol. 64, No. 4, pp. 633-644, DOI:10.1111/j.1365-313X.2010.04363.x, ISSN 0960-7412, XP055834430.

Gerasimova S.V., et al., "Genome Editing System CRISPR/CAS9 and Peculiarities of Its Application in Monocots," Russian Journal of Plant Physiology, Moscow, RU, Mar. 5, 2017, vol. 64, No. 2, pp. 141-155.

Harberd N.P., et al., "Genetics of Dominant Gibberellin-Insensitive Dwarfism in Maize," Genetics, Apr. 1989, vol. 121, pp. 827-838.

Hirai M., et al., "A novel locus for clubroot resistance in *Brassica rapa* and its linkage markers" Theor Appl Genet, Feb. 2004, vol. 108(4), pp. 639-643. doi: 10.1007/s00122-003-1475-x. Epub Oct. 1, 20030.

International Preliminary Report on Patentability for International Application No. PCT/US2018/044498, mailed Mar. 26, 2020, 23 Pages.

International Preliminary Report on Patentability for International Application No. PCT/US2020/064999, mailed Jun. 30, 2022, 11 Pages.

International Preliminary Report on Patentability for International Application No. PCT/US2022/013522, mailed Aug. 10, 2023, 9 Pages.

International Search Report and Written Opinion for International Application No. PCT/US2018/044498, mailed Nov. 6, 2018, 26 Pages.

Karim M.M., et al., "Two Clubroot-Resistance Genes, Rcr3 and Rcr9wa, Mapped in *Brassica rapa* Using Bulk Segregant RNA Sequencing," International Journal of Molecular Sciences, 2020, vol. 21, No. 14, p. 5033, XP093223878, ISSN: 1422-0067, pp. 1-15.

Lai J., et al., "Genome-wide Patterns of Genetic Variation Among Elite Maize Inbred Lines," Nature Genetics, 2010, vol. 42, No. 11, pp. 1027-1030.

Lawit S.J., et al., "Maize DELLA Proteins Dwarf Plant8 and Dwarf Plant9 as Modulators of Plant Development," Plant Cell Physiology, 2010, vol. 51, No. 11, pp. 1854-1868.

Matsumoto E., et al., "Linkage analysis of RFLP markers for clubroot resistance and pigmentation in Chinese cabbage (*Brassica rapa* ssp. *pekinensis*)" Kluwer Academic Publishers, 1998, pp. 79-86.

Mehraj H., et al., "Genetics of Clubroot and Fusarium Wilt Disease Resistance in *Brassica* Vegetables: The Application of Marker Assisted Breeding for Disease Resistance," Plants, Mar. 24, 2020, vol. 9, No. 6, pp. 1-15, XP055960524.

Mohr S.E., et al., "CRISPR Guide RNA Design for Research Applications," The FEBS Journal, 2016, vol. 283, pp. 3232-3238 (col. 1, Paragraph 1—p. 3232).

Murphy K., "The Influence of Plant Densities on Yields and Agronomic Performance of a Semi-dwarf and a Conventional Type Corn Hybrid in Southern Manitoba," Thesis, Master of Science in the Department of Plant Science, University of Manitoba, National Library of Canada, 1988, 105 Pages.

Neuffer, M.G., "Location, description and notes on other dominant mutants," Maize Genetics Cooperation News Letter, 1990, No. 64, pp. 51-52.

Pang W., et al., "Identification and Mapping of the Clubroot Resistance Gene CRd in Chinese Cabbage ( *Brassica rapa* ssp.

(56) References Cited

OTHER PUBLICATIONS

*pekinensis*)" Front Plant Sci, May 18, 2018, vol. 9:Articel.653, pp. 1-9. doi: 10.3389/fpls.2018.00653. eCollection 2018.

Partial Supplementary European Search Report for European Application No. 18856566.7, mailed Sep. 15, 2021, 13 Pages.

Paterson A.H., et al., "The Sorghum Bicolor Genome and the Diversification of Grasses," Nature, Jan. 29, 2009, vol. 457, No. 29, DOI: 10.1038/nature07723, pp. 551-556, XP009145526.

Peng J., et al., "Green Revolution'genes Encode Mutant Gibberellin Response Modulators," Nature, 1999, vol. 400, No. 6741, pp. 256-261.

Piao Z., et al., "Genetics of Clubroot Resistance in *Brassica* Species," Journal of Plant Growth Regulation, 2009, vol. 28, No. 3, pp. 252-264, XP019739174.

Piao Z.Y., et al., "SCAR and CAPS mapping of CRb, a gene conferring resistance to Plasmodiophora brassicae in Chinese cabbage ( *Brassica rapa* ssp. *pekinensis*)" Theor Appl Genet, May 2004, vol. 108(8), pp. 1458-1465. doi: 10.1007/s00122-003-1577-5. Epub Mar. 2, 2004.

Prykhozhij S.V., et al., "A Rapid and Effective Method for Screening, Sequencing and Reporter Verification of Engineered Frameshift Mutations in Zebrafish," Disease Models Mechanisms, Jun. 1, 2017, vol. 10, pp. 811-822.

Richards D.E., "How Gibberellin Regulates Plant Growth and Development: A Molecular Genetic Analysis of Gibberellin Signaling," Annual Review of Plant Biology, Jun. 2001, vol. 52, 67-88, 28 Pages.

Saito M., et., "Fine mapping of the clubroot resistance gene, Crr3, in *Brassica rapa*" Theor Appl Genet. Dec. 2006; vol. 114(1): pp. 81-91. doi: 10.1007/s00122-006-0412-1. Epub Oct. 13, 2006.

Sakamoto K., et al., "Mapping of isolate-speciWc QTLs for clubroot resistance in Chinese cabbage (*Brassica rapa* L. ssp. *pekinensis*)" Theor Appl Genet, Sep. 2008; vol. 117(5):759-67. doi: 10.1007/s00122-008-0817-0. Epub Jul. 9, 2008.

Sangoi L., et al., "Influence of Plant Height and of Leaf Number on Maize Production at High Plant Densities," Pesquisa Agropecuaria Brasileira, 1998, vol. 33, pp. 297-306, 11 Pages, Mar. 1, 1998.

Schaefer C.M., "Breeding Potential of Semi-Dwarf Corn for Grain and Forage in the Northern U.S. Corn Belt," Master's Thesis, University of Minnesota, Retrieved from the University of Minnesota Digital Conservancy, Oct. 2010, 38 Pages.

Schaefer C.M., et al., "Breeding Potential of Semidwarf Com for Grain and Forage in the Northern U.S. Corn Belt," Drop Science, Jul.-Aug. 2011, vol. 51, pp. 1637-1645, 10 Pages.

Suwabe K., "Identification of two loci for resistance to clubroot (*Plasmodiophora brassicae* Woronin) in *Brassica rapa* L." Theor Appl Genet. Oct. 2003; vol. 107(6): pp. 997-1002. doi: 10.1007/s00122-003-1309-x. Epub Sep. 3, 2003.

Svitashev S., et al., "Targeted Mutagenesis, Precise Gene Editing, and Site-Specific Gene Insertion in Maize using Cas9 and Guide RNA," Plant Physiology, 2015, vol. 169, No. 2, pp. 931-945.

Thornsberry J.M., et al., "Dwarf8 Polymorphisms Associate with Variation in Flowering Time," Nature Genetics, 2001, vol. 28, No. 3, pp. 286-289.

Timmermans M.C.P., et al., "The 46th Annual Maize Genetics Conference Meeting Report. Unlocking the Secrets of the Maize Genome," Plant Physiology, 2004, vol. 136, No. 1, pp. 2633-2640.

UNIPROT: RecName: "Full=DELLA Protein DWARF8," Short= Protein dwarf-8, Database Accession No. Q9ST48, May 1, 2022, Retrieved from URL: EBI.

Wang Y., et al., "Deletion of a Target Gene in Indica Rice via CRISPR/Cas9," Plant Cell Reports, 2017, vol. 36, pp. 1333-1343, Retrieved from URL: https://doi.org/10.1007/s00299-017-2158-4.

Wang Y. et al., "Revealing Physiological and Genetic Properties of a Dominant Maize Dwarf Dwarf11 (D11) by Integrative Analysis," Molecular Breeding, 2016, vol. 36: 31.

Willige R.C., et al., The DELLA Domain of GA INSENSITIVE Mediates the Interaction with the GA INSENSITIVE DWARF1A Gibberellin Receptor of Arabidopsis, The Plant Cell, 2007, vol. 19, pp. 1209-1220.

Winkler R.G., et al., "Physiological Genetics of the Dominant Gibberellin-Nonresponsive Maize Dwarfs, Dwarf8 and Dwarf9," Planta, 1994, vol. 193, No. 3, pp. 341-348.

\* cited by examiner

(A)
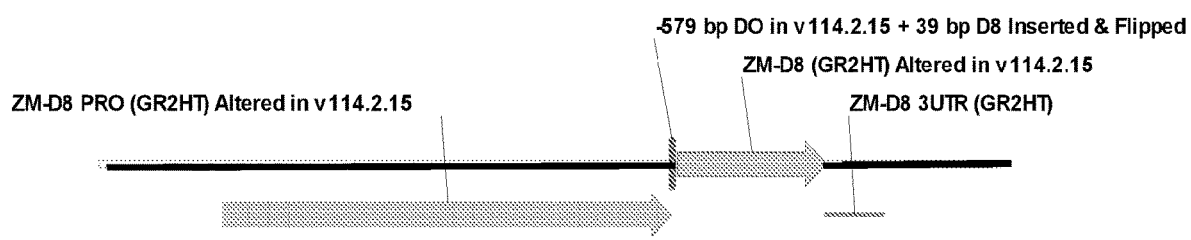
(B)
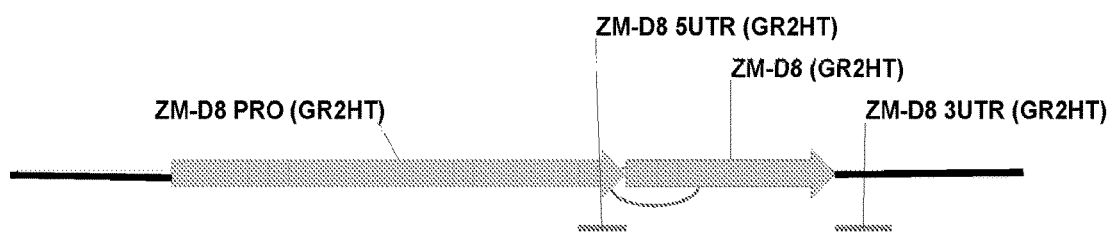

REDUCED STATURE MAIZE AND MADS-BOX TRANSCRIPTION FACTORS

CROSS-REFERENCE TO RELATED APPLICATIONS

This application claims the benefit of PCT Application Serial Number PCT/US2020/064999, filed Dec. 15, 2020, which claims the benefit of U.S. Provisional Application No. 62/949,206, filed Dec. 17, 2019, both of which are hereby incorporated herein by reference in their entireties.

REFERENCE TO SEQUENCE LISTING SUBMITTED ELECTRONICALLY

The official copy of the sequence listing is submitted electronically via EFS-Web as an ASCII formatted sequence listing with a file named "8197_ST25.txt" created on Dec. 17, 2019 and having a size of 39 kilobytes and is filed concurrently with the specification. The sequence listing contained in this ASCII formatted document is part of the specification and is herein incorporated by reference in its entirety.

FIELD

Embodiments disclosed herein relate to the field of plant molecular biology and agronomic traits.

BACKGROUND

Corn is an agriculturally important crop and serves as a food and feed source for animal, human, and industrial uses. Increased grain yield may be achieved in maize plants by a variety of ways, including expression of a transgene to increase grain yield in addition to improved breeding. Performance of a transgene in a plant including the agronomic parameters, may be impacted by a variety of factors such as the use of expression elements including promoter/regulatory elements, the genomic location of the insert sequence, copy number of the inserted transgene and genetic (germplasm) and environmental factors such as soil, temperature, light and moisture. The identification of constructs, testing of orthologs and transformation events that result in increased grain yield of a maize plant at a commercially relevant level in the field are the result of a substantial and significant developmental effort towards product advancement. Accordingly, it would be desirable to have maize plants that demonstrate increased grain yield.

SUMMARY

A corn plant comprising a stature reducing genetic modification and a yield enhancing genetic modification, wherein the yield enhancing genetic modification comprises a heterologous regulatory polynucleotide operably linked to a polynucleotide that encodes a polypeptide comprising an amino acid sequence that is at least 95% identical to SEQ ID NO: 1 and wherein the corn plant exhibits a plant height reduction of about 5% to about 50%, when compared to a control corn plant not comprising the stature reducing genetic modification. In certain embodiments, the stature reducing genetic modification is an introduced genetic modification in one or more genomic loci selected from the group consisting of: a polynucleotide encoding the D8 polypeptide; a polynucleotide encoding a MYB transcription factor expression or activity; MYB transcription factor genomic locus comprises a brachytic 1 (br1) allele in maize; a component involved in a biological pathway related to gibberellic acid biosynthesis or gibberellic acid signaling; a component involved in a biological pathway related to auxin transport, auxin signaling; a component involved in a biological pathway related to brassinosteroid biosynthesis or signaling; and Brachytic 2 (Br2) allele.

A seed produced from the corn plant wherein a progeny from the seed exhibits increased yield and reduced stature when compared to the control plant. A corn plant, seed, cell or part thereof comprising event DP-202216-6 and exhibiting reduced stature, wherein a representative sample of seed of said corn event has been deposited with American Type Culture Collection (ATCC) with Accession No. PTA-124653.

A unit of corn seeds, the unit comprising a mixture of seeds wherein the mixture comprises about 10% to about 75% seeds exhibiting reduced stature due to an introduced genetic modification and exhibiting increased yield due to increased expression of a polynucleotide that encodes a polypeptide comprising an amino acid sequence that is at least 95% identical to SEQ ID NO: 1, when compared to a control plant.

A method of increasing planting density of corn plants comprising a heterologous regulatory polynucleotide operably linked to a polynucleotide that encodes a polypeptide comprising an amino acid sequence that is at least 95% identical to SEQ ID NO: 1, the method comprising:

a) providing corn plants wherein the expression of the polynucleotide encoding the polypeptide is increased when compared to a control plant;

b) reducing plant height by introducing a genetic modification that results in reduced stature of the corn plants; and c) planting the corn plants at a planting density of about 30,000 to about 75,000 plants per acre.

In certain embodiments, the planting density is at least 50,000 plants; 55,000 plants; 58,000 plants; 60,000 plants; 62,000 plants; 64,000 plants. In certain aspects, the corn plants comprise a mutation in a genomic region encoding D8 polypeptide or reduced expression of the polynucleotide encoding D8 polypeptide. In certain aspects, the corn plants are planted in a plurality of rows having a row width of about 8 inches to about 30 inches. In certain aspects, the corn plants yield an average of about 3 bu/acre compared to control corn plants.

A method of increasing nitrogen use efficiency of a population of corn plants per unit of applied nitrogen, the method comprising: providing the population of corn plants, wherein the expression of a polynucleotide that encodes a polypeptide comprising an amino acid sequence that is at least 95% identical to SEQ ID NO: 1 is increased due to a genetic modification compared to a control plant; modifying the plant height of the population of the corn plants by introducing a genetic modification that results in reduced stature of the population of the corn plants; and growing the population of plants in a crop growing environment where the applied nitrogen is about 10% to about 50% less than an application rate of about 100 lbs to about 400 lbs of nitrogen per acre. In certain aspects, the population of corn plants exhibit an increase in nitrogen use efficiency of at least about 5% when compared to the control plant. In certain aspects, the nitrogen use efficiency is increased by applying late season nitrogen, wherein at least about 25% of total nitrogen applied is applied on or after V8-V12 stage.

A method of improving an agronomic characteristic of a population of corn plants grown in a field, the method comprising: providing the population of corn plants, wherein the expression of a polynucleotide that encodes a polypeptide comprising an amino acid sequence that is at least 95% identical to SEQ ID NO: 1 is increased due to a genetic modification compared to a control plant; modifying the plant height of the population of the corn plants by introducing a genetic modification that results in reduced stature of the population of the corn plants; and growing the population of plants in a crop growing environment, wherein an agronomic characteristic of the population of the corn plants is improved compared to a control population of plants. In certain aspects, the corn plants exhibit an increase in standability when compared to the control plant. In certain aspects, the population of corn plants exhibit an increase in early season canopy thereby resulting in improved weed control and/or less applied herbicide per acre. In certain aspects, the population of corn plants exhibit a decrease in early season disease. In certain aspects, the population of corn plants leave reduced net residue per bushel of grain yield after harvest.

A method for reducing production costs of corn hybrids, the method comprising sexually crossing a first parent corn plant with a second parent corn plant, wherein said first parent corn plant comprises event DP-202216-6 DNA and exhibits reduced plant height compared to the second parent corn, thereby producing a plurality of hybrid progeny plants in a field. In certain aspects, the first corn plant is female inbred. In certain aspects, the hybrid yield is increased by at least 5% compared to a control plant.

A reduced stature corn seed includes Event DP-202216-6, wherein a representative sample of corn event DP-202216-6 seed of has been deposited with American Type Culture Collection (ATCC) with Accession No. PTA-124653.

In an embodiment, a corn plant comprises increased and extended expression of a monocot MADS box polynucleotide that increases yield and one or more genetic modifications targeting one or more distinct genomic loci that are involved in plant height reduction. In an embodiment, the plant height is reduced by about 5% to about 30% compared to the control plant. In an embodiment, such plant comprises an average leaf length to width ratio reduced at V6-V8 growth stages. In an embodiment, such plant height reduction does not substantially affect flowering time. In an embodiment, the flowering time does not change by more than about 5-10 CRM or plus or minus 10% GDU or 125-250 GDU, compared to a control plant not comprising the modifications or the increased MADS polypeptide expression, wherein 25 GDU is equivalent to about 1 day and 1 CRM is about 1 day. In an embodiment, the plant height reduction does not substantially alter root architecture of the plant or does not significantly increase root lodging, compared to a control plant not comprising the modifications. In an embodiment, the plant is substantially tolerant to lodging as measured at a single plant level or at an increased planting density, compared to a control plant or control population of plants. In an embodiment, the plant comprises up to about 10% less number of leaves compared to the control plant. In an embodiment, the plant is maize and the plant height reduction is characterized by the shortening of distance between one or more internodes that are present above or below a female reproductive part of the maize plant. Modified maize plants, whose average internode lengths are reduced compared to the wild-type plants are provided. For example, average internode length (2nd internode length and/or 4th internode length relative to the position of the ear) that is at least 5%, 10%, 15%, 20%, 25%, 30%, 35%, 40%, 45%, 50%, 55%, 60%, 65%, 70%, 75% less than the same or average internode length of a wild-type or control plant are provided. The 2nd internode" refers to the second internode below the ear of the corn plant, likewise, the "4th internode" refers to the fourth internode below the ear of the corn plant.

Corn plants with increased expression of SEQ ID NO: 1 are provided that have (i) a plant height that is at least 5%, 10%, 15%, 20%, 25%, 30%, 35%, 40%, 45%, 50%, 55%, 60%, 65%, 70%, 75% less than the height of a wild-type or control plant, and/or (ii) a stem or stalk diameter that is at least 5%, 5%, 10%, 15%, 20%, 25%, 30%, 35%, 40%, 45%, 50%, 55%, 60%, 65%, 70%, 75%, 80% greater than the stem diameter of the wild-type or control plant.

In an embodiment, in addition to an increase in field grain yield due to extended expression of AG099, one or more of the following agronomic characteristics of the plant is also increased or reduced: harvest index of the plant is increased; leaf area is increased; leaf number above the ear is reduced; ratio of the plant ear height over the plant height is increased; and the yield is increased at higher planting density, as compared to a control plant not comprising the mutations.

In an embodiment, the ear height as measured to the maize plant height is substantially similar or slightly reduced to the ear height measured relative to the control plant height, wherein the plant comprises one or more genetic modifications that increase expression of an endogenous polynucleotide encoding a polypeptide that is at least 95% identical to SEQ ID NO: 1. In an embodiment, the height reducing genetic modifications target the genomic locus such that more than one genetic modifications are present within (a) the same coding region; (b) non-coding region; (c) regulatory sequence; or (d) untranslated region, of an endogenous polynucleotide encoding a polypeptide that is involved in plant height.

A reduced stature maize plant stably transformed with a recombinant polynucleotide sequence encoding a polypeptide comprising an amino sequence that is at least 90%, 93% 95%, 97%, 98% or 99% identical to SEQ ID NO: 1, wherein the maize plant exhibits increased grain yield compared to a control maize plant not containing the recombinant polynucleotide. In some embodiments, the recombinant polynucleotide is operably linked to a weak heterologous constitutive regulatory element. In some embodiments, the grain yield is at least about three bushels/acre when compared to the control maize plant, wherein the maize plant and the control maize plant are grown in a field under normal crop growing conditions. In some embodiments, the grain yield in the field range from about 2 to about 8 bu/acre when compared to the control population of maize plants grown in a population density of about 20,000 to about 60,000 plants per acre. In some embodiments, the weak heterologous constitutive regulatory element is a maize GOS2 promoter. In some embodiments, the amino acid sequence is at least 95% identical to SEQ ID NO: 1 and the maize plant comprises a polynucleotide encoding a polypeptide that provides herbicide tolerance and a polynucleotide that encodes a polypeptide or an RNA sequence that provides resistance to one or more insect pests. Maize seed produced from the maize plant described herein exhibit yield improvement characteristics and reduced stature. In an embodiment, the regulatory element comprises a heterologous intron element.

A method of increasing grain yield of a short stature maize plant, the method comprising expressing a polynucleotide sequence encoding a polypeptide that is at least 90%, 93% 95%, 97%, 98% or 99% identical to SEQ ID NO: 1, wherein the polynucleotide is operably linked to a heterologous regulatory sequence; and growing the maize plant in a field to increase grain yield compared to a control maize plant not containing the polynucleotide operably linked to the heterologous regulatory sequence.

A method of producing a seed, the method comprising the following:

(a) crossing a first plant with a second plant, wherein at least one of the first plant and the second plant comprises a recombinant DNA construct, wherein the recombinant DNA construct comprises (i) a polynucleotide operably linked to at least one regulatory element, wherein the polynucleotide encodes a MADS protein having an amino acid sequence of at least 90% sequence identity, based on the Clustal V or Clustal W method of alignment, when compared to SEQ ID NO: 1 or (ii) a genetic component responsive for reduced stature and wherein the second plant is of shorter stature or reduced height; and (b) selecting a seed of the crossing of step (a), wherein the seed comprises the recombinant DNA construct.

A reduced stature plant grown from the seed produced by the method described herein, wherein the plant exhibits increased yield, when compared to a control plant not comprising the recombinant DNA construct.

In some embodiments, a method of selecting a plant that exhibits increased yield the method comprises:

(a) obtaining a reduced stature plant, wherein the plant comprises in its genome a recombinant DNA construct comprising a polynucleotide operably linked to at least one regulatory element, wherein said polynucleotide encodes a MADS protein having an amino acid sequence of at least 90% sequence identity, based on the Clustal V or Clustal W method of alignment, when compared to SEQ ID NO: 1 and a genetic element that reduces plant height;

(b) growing the plant in a field under conditions wherein the polynucleotide is expressed; and (c) selecting the plant of part that exhibits increased yield when compared to a control plant not comprising the recombinant DNA construct and exhibits reduction in plant height compared to the control plant.

A reduced stature maize plant that exhibits increased expression of an endogenous polynucleotide encoding a polypeptide comprising a sequence that is at least 95% identical to SEQ ID NO: 1, wherein the increased expression is due to a heterologous regulatory element. In some embodiments, the heterologous regulatory element is a plant-derived enhancer element. In some embodiments, the heterologous regulatory element is a weak constitutive promoter element. In some embodiments, the maize plant is an inbred or a hybrid plant.

In some embodiments, the reduced stature maize plant includes a second polypeptide that provides herbicide tolerance and a third polypeptide that provides insect resistance.

A reduced stature corn plant, seed, cell or part thereof includes event DP-202216-6. A reduced stature corn plant, seed, cell or part thereof includes event DP-202216-6, wherein a representative sample of seed of said corn event has been deposited with American Type Culture Collection (ATCC) with Accession No. PTA-124653. In some embodiments, the plant part is selected from the group consisting of pericarp, pollen, ovule, flower, grain, shoot, root, stalk, silk, tassel, ear, and leaf tissue. A biological sample derived from a reduced stature corn event DP-202216-6 plant, tissue, or seed, wherein a representative sample of said corn event DP-202216-6 seed of has been deposited with American Type Culture Collection (ATCC) with Accession No. PTA-124653. In some embodiments, the biological sample comprises plant, tissue, or portions of seed, pericarp of seed of transgenic corn event DP-202216-6. In some embodiments, the biological sample is a DNA sample extracted from the transgenic corn plant event DP-202216-6. In some embodiments, the first inbred corn line is a female parent or the first inbred corn line is a male parent.

A method for producing a reduced stature corn plant that exhibits increased grain yield in a field, the method comprising: sexually crossing a first parent corn plant with a second parent corn plant, wherein said first or second parent corn plant comprises Event DP-202216-6 DNA or reduced stature, thereby producing a plurality of first generation progeny plants; selfing the first generation progeny plant, thereby producing a plurality of second generation progeny plants; and selecting from the second generation progeny plants that comprise the event DP-202216-6, a plant that exhibits increased grain yield in the field compared to a control corn plant not comprising the event DP-202216-6. In some embodiments, the event DP-202216-6 comprises a recombinant DNA construct and wherein the event DP-202216-6 comprises encodes a polypeptide that is at least 99% identical to SEQ ID NO: 1.

A method of producing hybrid corn seeds comprising:
a) sexually crossing a first inbred corn line comprising the DNA construct described herein with a second inbred line not comprising the DNA construct, but exhibits reduced stature; and
b) harvesting the hybrid seed produced thereby.

In some embodiments, the step of backcrossing includes backcrossing the second generation progeny plant that comprises reduced stature corn event DP-202216-6 to the parent plant that lacks the corn event DP-202216-6, thereby producing a backcross progeny plant that exhibits increased grain yield compared to a control corn plant not comprising the event DP-202216-6.

A method of increasing grain yield of a population of maize plants in a field, the method comprising growing a population of reduced stature maize plants comprising Event DP-202216-6 in a field and thereby increasing grain yield of the population of maize plants compared to a control plant not comprising the Event DP-202216-6. In some embodiments, the population of reduced stature maize plants are grown under abiotic stress. In some embodiments, the abiotic stress is low nitrogen. In some embodiments, when grown under low nitrogen conditions, the population of reduced stature maize plants comprising the Event DP-202216-6 exhibits yield stability compared to the control population of plants grown under low nitrogen. In some embodiments, the low nitrogen is about 25% to about 75% reduction in the amount of nitrogen normally applied to grow hybrid corn plants in the field. In some embodiments, the reduction in nitrogen applied to field ranges from about 5% to about 10%, 20%, 30%, 40%, 50%, 60% or 70% compared to a normal application of nitrogen.

According to another embodiment, methods of producing a corn plant that comprise the steps of: (a) sexually crossing a first parental corn line comprising the expression cassettes disclosed herein, which increase yield, and a second parental corn line that lacks such constructs but exhibits reduced stature, thereby producing a plurality of progeny plants; and (b) selecting a progeny plant that shows increase in yield. Such methods may optionally include the further step of back-crossing the progeny plant to the second parental corn line to producing a true-breeding corn plant that exhibits yield increase.

In an aspect, a method of growing a population of corn plants in a field, the method comprising providing seeds that grow as corn plants that comprise (a) introduced genetic modification that increases and extends the expression of a polynucleotide that encodes a polypeptide comprising an amino acid sequence that encodes a MADS-box monocot transcription factor; (b) one or more introduced genetic modifications that reduced plant height by about 10% to about 50% compared to a control corn plant not comprising the height reducing genetic modifications; and (c) root depth that is at least 50% of the root depth of a control plant not comprising the height reducing genetic modifications. In an aspect, the polypeptide comprises an amino acid sequence that is at least 90% identical to SEQ ID NO: 1. In an aspect, the field comprises about 40,000 to about 70,000 corn plants per acre. In an aspect, the field comprises a root growth enhancing agricultural composition. In an aspect, the agricultural composition is a biological applied as a seed treatment or soil applied. In an aspect, the population of plants comprise one or more introduced genetic modification that increases root growth.

In an aspect, a method of managing disease in a field comprising short stature, high yielding corn plants planted at a high planting density, the method comprising (i) providing seeds that grow as corn plants that comprise (a) introduced genetic modification that increases and extends the expression of a polynucleotide that encodes a polypeptide comprising an amino acid sequence that encodes a MADS-box monocot transcription factor; and (b) one or more introduced genetic modifications that reduced plant height by about 10% to about 50% compared to a control corn plant not comprising the height reducing genetic modifications; and (ii) providing a pesticide composition at an effective rate such that the pesticide is available to control disease occurrence during mid or late growth season in the field, wherein the corn plants are planted at a planting density of at least 45,000 plants per acre. In an aspect, the pesticide is applied as an extended release pesticide that controls one or more corn diseases. In an aspect, the pesticide is applied over-the-top of the corn plants. In an aspect, the pesticide is applied as a seed treatment. In an aspect, the corn plants comprise one or more introduced genetic modifications that provide resistance to one or more diseases that occur within short stature, high-yielding and at high planting density. In an aspect, the corn plants comprise a transgene that provides resistance to one or more pests. In an aspect, the corn plants are subject to an abiotic stress. In an aspect, the corn plants are subject to insect pressure.

BRIEF DESCRIPTION OF THE DRAWINGS

FIG. 1 is a schematic illustration showing N-terminal deletion genome edits to create short stature/semi-dwarf corn plants. (A) shows the illustration where a deletion of 579 bp with insertion of flipped 39 bp of 5'UTR & 5 bp CDS. The genomic length after the edit is 8170 bp. (B) shows the genomic region of the wild-type, approximately about 9000 bp in length.

BRIEF DESCRIPTION OF THE SEQUENCES

The disclosure can be more fully understood from the following detailed description and the accompanying drawings and Sequence Listing that form a part of this application.

The sequence descriptions summarize the Sequence Listing attached hereto, which is hereby incorporated by reference. The Sequence Listing contains one letter codes for nucleotide sequence characters and the single and three letter codes for amino acids as defined in the IUPAC-IUB standards described in Nucleic Acids Research 13:3021-3030 (1985) and in the Biochemical Journal 219(2):345-373 (1984).

TABLE 1

Sequence Listing Description

| SEQ ID NO: | Description |
| --- | --- |
| 1 | Maize MADS-box protein 28 |
| 2 | Maize MADS-box protein 28 DNA |
| 3 | ZM-D8_CDS_B73 |
| 4 | ZM-D8_GENE_B73 |
| 5 | ZM-D8_PRO_B73 |
| 6 | ZM-D8-Peptide-B73 |
| 7 | ZM-BR1_CDS_B73 |
| 8 | ZM-BR1_PRO_B73 |
| 9 | Peptide Transcription regulator HTH (ZmBr1) |

DETAILED DESCRIPTION

As used herein the singular forms "a", "and", and "the" include plural referents unless the context clearly dictates otherwise. Thus, for example, reference to "a cell" includes a plurality of such cells and reference to "the protein" includes reference to one or more proteins and equivalents thereof, and so forth. All technical and scientific terms used herein have the same meaning as commonly understood to one of ordinary skill in the art to which this disclosure belongs unless clearly indicated otherwise.

The disclosure and content of International Patent Application Publication No. WO2019055141A (application serial number PCT/US2018/044498), as it relates to stature modification, are herein incorporated by reference in its entirety.

Compositions of this disclosure include a representative sample of seeds which was deposited as Patent Deposit No. PTA-124653 and plants, plant cells, and seed derived therefrom. Applicant(s) have made a deposit of at least 2500 seeds of maize event DP-202216-6 (Patent Deposit No. PTA-124653) with the American Type Culture Collection (ATCC), Manassas, Va. 20110-2209 USA, on Jan. 12, 2018 and were accepted on Jan. 18, 2018. These deposits were made under the terms of the Budapest Treaty and will be maintained under the terms of the Budapest Treaty on the International Recognition of the Deposit of Microorganisms for the Purposes of Patent Procedure. The seeds deposited with the ATCC on Jan. 12, 2018 were taken from a representative sample deposit maintained by Pioneer Hi-Bred International, Inc., 7250 NW 62$^{nd}$ Avenue, Johnston, Iowa 50131-1000. Access to this ATCC deposit will be available during the pendency of the application to the Commissioner of Patents and Trademarks and persons determined by the Commissioner to be entitled thereto upon request, in accordance with applicable laws and regulations. All restrictions upon availability to the public will be irrevocably removed upon granting of the patent. Upon issuance of a patent, this deposit of seed of maize Event DP-202216-6 is intended to meet all the necessary requirements of 37 C.F.R. §§ 1.801-1.809, and will be maintained in the ATCC depository, which is a public depository, for a period of 30 years, or 5 years after the most recent request, or for the enforceable life of the patent, whichever is longer, and will be replaced if it becomes nonviable during that period. Upon allowance of any claims in the application, the Applicant(s) will make this deposit available to the public pursuant to the Budapest Treaty. Unauthorized seed multiplication prohibited. The seed may be regulated under one or more applicable National, State or other local regulations and ordinances imposed by one or more competent governmental agencies.

As used herein, the term "corn" means *Zea mays* or maize and includes all plant varieties that can be bred with corn, including wild maize species.

As used herein, the terms "insect resistant" and "impacting insect pests" refers to effecting changes in insect feeding, growth, and/or behavior at any stage of development, including but not limited to: killing the insect; retarding growth; reducing reproductive capability; inhibiting feeding; and the like.

As used herein, the terms "pesticidal activity" and "insecticidal activity" are used synonymously to refer to activity of an organism or a substance (such as, for example, a protein) that can be measured by numerous parameters including, but not limited to, pest mortality, pest weight loss, pest attraction, pest repellency, and other behavioral and physical changes of a pest after feeding on and/or exposure to the organism or substance for an appropriate length of time. For example, "pesticidal proteins" are proteins that display pesticidal activity by themselves or in combination with other proteins.

As used herein, "insert DNA" refers to the heterologous DNA within the expression cassettes used to transform the plant material while "flanking DNA" can exist of either genomic DNA naturally present in an organism such as a plant, or foreign (heterologous) DNA introduced via the transformation process which is extraneous to the original insert DNA molecule, e.g. fragments associated with the transformation event. A "flanking region" or "flanking sequence" as used herein refers to a sequence of at least 20 bp, for some embodiments, at least 50 bp, and up to 5000 bp, which is located either immediately upstream of and contiguous with or immediately downstream of and contiguous with the original foreign insert DNA molecule.

In an embodiment, the junction sequences of Event DP-202216-6, for example, may include polymorphisms (e.g., SNPs) or mutations that may occur spontaneously in the endogenous genomic region of the junction sequence. These may include insertion, deletion or substitution of one or more nucleotides in the junction sequence. Polynucleotide sequences that are at least 90%, 91%, 92%, 93%, 94%, 95%, 96%, 97%, 98%, and 99% to one or more of the junction sequences.

As used herein, "heterologous" in reference to a nucleic acid sequence is a nucleic acid sequence that originates from a foreign species, or, if from the same species, is substantially modified from its native form in composition and/or genomic locus by deliberate human intervention. For example, a promoter operably linked to a heterologous nucleotide sequence can be from a species different from that from which the nucleotide sequence was derived, or, if from the same species, the promoter is not naturally found operably linked to the nucleotide sequence. A heterologous protein may originate from a foreign species, or, if from the same species, is substantially modified from its original form by deliberate human intervention.

The term "regulatory element" refers to a nucleic acid molecule having gene regulatory activity, i.e. one that has the ability to affect the transcriptional and/or translational expression pattern of an operably linked transcribable polynucleotide. The term "gene regulatory activity" thus refers to the ability to affect the expression of an operably linked transcribable polynucleotide molecule by affecting the transcription and/or translation of that operably linked transcribable polynucleotide molecule. Gene regulatory activity may be positive and/or negative and the effect may be characterized by its temporal, spatial, developmental, tissue, environmental, physiological, pathological, cell cycle, and/or chemically responsive qualities as well as by quantitative or qualitative indications.

"Promoter" refers to a nucleotide sequence capable of controlling the expression of a coding sequence or functional RNA. In general, a coding sequence is located 3' to a promoter sequence. The promoter sequence comprises proximal and more distal upstream elements, the latter elements are often referred to as enhancers. Accordingly, an "enhancer" is a nucleotide sequence that can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. It is understood by those skilled in the art that different regulatory elements may direct the expression of a gene in different tissues or cell types, or at different stages of development, or in response to different environmental conditions. Promoters that cause a nucleic acid fragment to be expressed in most cell types at most times are commonly referred to as "constitutive promoters".

A DNA construct is an assembly of DNA molecules linked together that provide one or more expression cassettes. The DNA construct may be a plasmid that is enabled for self-replication in a bacterial cell and contains various endonuclease enzyme restriction sites that are useful for introducing DNA molecules that provide functional genetic elements, i.e., promoters, introns, leaders, coding sequences, 3' termination regions, among others; or a DNA construct may be a linear assembly of DNA molecules, such as an expression cassette. The expression cassette contained within a DNA construct comprises the necessary genetic elements to provide transcription of a messenger RNA. The expression cassette can be designed to express in prokaryote cells or eukaryotic cells. Expression cassettes of the embodiments are designed to express in plant cells.

The DNA molecules disclosed herein are provided in expression cassettes for expression in an organism of interest. The cassette will include 5' and 3' regulatory sequences operably linked to a coding sequence. "Operably linked" means that the nucleic acid sequences being linked are contiguous and, where necessary to join two protein coding regions, contiguous and in the same reading frame. Operably linked is intended to indicate a functional linkage between a promoter and a second sequence, wherein the promoter sequence initiates and mediates transcription of the DNA sequence corresponding to the second sequence. The cassette may additionally contain at least one additional gene to be co-transformed into the organism. Alternatively, the additional gene(s) can be provided on multiple expression cassettes or multiple DNA constructs.

The expression cassette may include in the 5' to 3' direction of transcription: a transcriptional and translational initiation region, a coding region, and a transcriptional and translational termination region functional in the organism serving as a host. The transcriptional initiation region (i.e., the promoter) may be native or analogous, or foreign or heterologous to the host organism. Additionally, the promoter may be the natural sequence or alternatively a synthetic sequence. The expression cassettes may additionally contain 5' leader sequences in the expression cassette construct. Such leader sequences can act to enhance translation.

A transgenic "event" is produced by transformation of plant cells with a heterologous DNA construct(s), including a nucleic acid expression cassette that comprises a transgene of interest, the regeneration of a population of plants resulting from the insertion of the transgene into the genome of the plant, and selection of a particular plant characterized by insertion into a particular genome location. An event is characterized phenotypically by the expression of the transgene. At the genetic level, an event is part of the genetic makeup of a plant. The term "event" also refers to progeny produced by a sexual outcross between the transformant and another variety that include the heterologous DNA. Even after repeated back-crossing to a recurrent parent, the inserted DNA and flanking DNA from the transformed parent is present in the progeny of the cross at the same chromosomal location. The term "event" also refers to DNA from the original transformant comprising the inserted DNA and flanking sequence immediately adjacent to the inserted DNA that would be expected to be transferred to a progeny that receives inserted DNA including the transgene of interest as the result of a sexual cross of one parental line that includes the inserted DNA (e.g., the original transformant and progeny resulting from selfing) and a parental line that does not contain the inserted DNA.

Corn plant containing event DP-202216-6 may be bred by first sexually crossing a first parental corn plant consisting of a corn plant grown from event DP-202216-6 corn plant and progeny thereof derived from transformation with the expression cassettes of the embodiments that increase yield when compared to a control plant, and a second parental corn plant that does not have such constructs, thereby producing a plurality of first progeny plants; and then selecting a first progeny plant that demonstrates yield increase; and selfing the first progeny plant, thereby producing a plurality of second progeny plants; and then selecting from the second progeny plants plant with yield increase.

As used herein, the term "plant" includes reference to whole plants, parts of plants, plant organs (e.g., leaves, stems, roots, etc.), seeds, plant cells, and progeny of same. In some embodiments, parts of transgenic plants comprise, for example, plant cells, protoplasts, tissues, callus, embryos as well as flowers, stems, fruits, leaves, and roots originating in transgenic plants or their progeny previously transformed with a DNA molecule disclosed herein, and therefore consisting at least in part of transgenic cells.

As used herein, the term "plant cell" includes, without limitation, seeds, suspension cultures, embryos, meristematic regions, callus tissue, leaves, roots, shoots, gametophytes, sporophytes, pollen, and microspores. The class of plants that may be used is generally as broad as the class of higher plants amenable to transformation techniques, including both monocotyledonous and dicotyledonous plants.

The present disclosure provides a commodity product that is derived from a corn plant comprising event DP-202216-6. As used herein, a "commodity product" generally refers to any composition or material that includes material derived or processed from a plant, seed, plant cell, or plant part comprising event DP-202216-6. Commodity products may be viable (e.g., seeds) or nonviable (e.g., corn meal). Nonviable commodity products include but are not limited to nonviable seeds and grains; processed seeds, seed parts, and plant parts; dehydrated plant tissue, frozen plant tissue, and processed plant tissue; seeds and plant parts processed for animal feed for terrestrial and/or aquatic animal's consumption, oil, meal, flour, flakes, bran, fiber, milk, cheese, paper, cream, wine, ethanol, and any other food for human consumption; and biomasses and fuel products. Viable commodity products include but are not limited to seeds and plant cells.

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include *Agrobacterium*-mediated transformation (De Blaere et al. (1987) *Meth. Enzymol.* 143:277) and particle-accelerated or "gene gun" transformation technology (Klein et al. (1987) *Nature* (London) 327:70-73; U.S. Pat. No. 4,945,050, incorporated herein by reference). Additional transformation methods are disclosed below.

As used herein, the term "progeny" in the context of DP-202216-6 denotes the offspring of any generation of a parent plant which comprises corn event DP-202216-6.

Isolated polynucleotides disclosed herein may be incorporated into recombinant constructs, typically DNA constructs, which are capable of introduction into and replication in a host cell. Such a construct may be a vector that includes a replication system and sequences that are capable of transcription and translation of a polypeptide-encoding sequence in a given host cell. A number of vectors suitable for stable transfection of plant cells or for the establishment of transgenic plants have been described in, e.g., Pouwels et al., (1985; Supp. 1987) *Cloning Vectors: A Laboratory Manual*, Weissbach and Weissbach (1989) *Methods for Plant Molecular Biology*, (Academic Press, New York); and Flevin et al., (1990) *Plant Molecular Biology Manual*, (Kluwer Academic Publishers). Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

During the process of introducing an insert into the genome of plant cells, it is not uncommon for some deletions or other alterations of the insert and/or genomic flanking sequences to occur. Thus, the relevant segment of the plasmid sequence provided herein might comprise some minor variations. The same is true for the flanking sequences provided herein. Thus, a plant comprising a polynucleotide having some range of identity with the subject flanking and/or insert sequences is within the scope of the subject disclosure. Identity to the sequence of the present disclosure may be a polynucleotide sequence having at least 65% sequence identity, for some embodiments at least 70% sequence identity, for some embodiments at least 75% sequence identity, for some embodiments at least 80% identity, and for some embodiments at least 85% 86%, 87%, 88%, 89%, 90%, 91%, 92%, 93%, 94%, 95%, 96%, 97%, 98%, 99%, 99.5% sequence identity with a sequence exemplified or described herein. Hybridization and hybridization conditions as provided herein can also be used to define such plants and polynucleotide sequences of the subject disclosure. The sequence which comprises the flanking sequences plus the full insert sequence can be confirmed with reference to the deposited seed.

A "probe" is an isolated nucleic acid to which is attached a conventional detectable label or reporter molecule, e.g., a radioactive isotope, ligand, chemiluminescent agent, or enzyme. Such a probe is complementary to a strand of a target nucleic acid, for example, to a strand of isolated DNA from corn event DP-202216-6 whether from a corn plant or from a sample that includes DNA from the event. Probes may include not only deoxyribonucleic or ribonucleic acids but also polyamides and other probe materials that bind specifically to a target DNA sequence and can be used to detect the presence of that target DNA sequence.

"Primers" are isolated nucleic acids that anneal to a complementary target DNA strand by nucleic acid hybridization to form a hybrid between the primer and the target DNA strand, then extended along the target DNA strand by a polymerase, e.g., a DNA polymerase. Primer pairs refer to their use for amplification of a target nucleic acid sequence, e.g., by PCR or other conventional nucleic-acid amplification methods. "PCR" or "polymerase chain reaction" is a technique used for the amplification of specific DNA segments (see, U.S. Pat. Nos. 4,683,195 and 4,800,159; herein incorporated by reference).

A nucleic acid molecule is said to be the "complement" of another nucleic acid molecule if they exhibit complete complementarity or minimal complementarity. As used herein, molecules are said to exhibit "complete complementarity" when every nucleotide of one of the molecules is complementary to a nucleotide of the other. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions. Conventional stringency conditions are described by Sambrook et al., 1989, and by Haymes et al., In: *Nucleic Acid Hybridization, a Practical Approach*, IRL Press, Washington, D.C. (1985), departures from complete complementarity are therefore permissible, as long as such departures do not completely preclude the capacity of the molecules to form a double-stranded structure. In order for a nucleic acid molecule to serve as a primer or probe it needs to be sufficiently complementary in sequence to be able to form a stable double-stranded structure under the particular solvent and salt concentrations employed.

In hybridization reactions, specificity is typically the function of post-hybridization washes, the relevant factors being the ionic strength and temperature of the final wash solution. The thermal melting point ($T_m$) is the temperature (under defined ionic strength and pH) at which 50% of a complementary target sequence hybridizes to a perfectly matched probe. For DNA-DNA hybrids, the $T_m$ can be approximated from the equation of Meinkoth and Wahl (1984) *Anal. Biochem.* 138:267-284: $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. $T_m$ is reduced by about 1° C. for each 1% of mismatching; thus, $T_m$, hybridization, and/or wash conditions can be adjusted to hybridize to sequences of the desired identity. For example, if sequences with >90% identity are sought, the $T_m$ can be decreased 10° C. Generally, stringent conditions are selected to be about 5° C. lower than the $T_m$ for the specific sequence and its complement at a defined ionic strength and pH. However, severely stringent conditions can utilize a hybridization and/or wash at 1, 2, 3, or 4° C. lower than the $T_m$; moderately stringent conditions can utilize a hybridization and/or wash at 6, 7, 8, 9, or 10° C. lower than the $T_m$; low stringency conditions can utilize a hybridization and/or wash at 11, 12, 13, 14, 15, or 20° C. lower than the $T_m$.

Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology Hybridization with Nucleic Acid Probes*, Part I, Chapter 2 (Elsevier, New York); and Ausubel et al., eds. (1995) and Sambrook et al. (1989).

The principle of hybridization analysis is that a single-stranded DNA or RNA molecule of a known sequence (e.g., the probe) can base-pair to a second DNA or RNA molecule that contains a complementary sequence (the target), with the stability of the hybridization depending on the extent of base pairing that occurs under the conditions tested. Appropriate stringency conditions for DNA hybridization, include for example, 6× sodium chloride/sodium citrate (SSC) at about 45° C., followed by a wash of 2.0×SSC at 50° C., are known to those skilled in the art or can be found in Current Protocols in Molecular Biology, John Wiley & Sons, N.Y. (1989), 6.3.1-6.3.6. For example, the salt concentration in the wash step can be selected from a low stringency of about 2.0×SSC at 50° C. to a high stringency of about 0.2×SSC at 50° C. or up to 0.1×SSC or 0.2×SSC, at 55° C. or 65° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable (e.g., time) is changed. In one embodiment, a nucleic acid of the present disclosure will specifically hybridize to one or more of the nucleic acid molecules or complements or fragments thereof under high stringency conditions. The hybridization of the probe to the target DNA molecule can be detected by methods known to those skilled in the art. These can include, but are not limited to, fluorescent tags, radioactive tags, antibody-based tags, and chemiluminescent tags.

In some embodiments, a complementary sequence has the same length as the nucleic acid molecule to which it hybridizes. In some embodiments, the complementary sequence is 1, 2, 3, 4, 5, 6, 7, 8, 9, or 10 nucleotides longer or shorter than the nucleic acid molecule to which it hybridizes. In some embodiments, the complementary sequence is 1%, 2%, 3%, 4%, or 5% longer or shorter than the nucleic acid molecule to which it hybridizes. In some embodiments, a complementary sequence is complementary on a nucleotide-for-nucleotide basis, meaning that there are no mismatched nucleotides (each A pairs with a T and each G pairs with a C). In some embodiments, a complementary sequence comprises 1, 2, 3, 4, 5, 6, 7, 8, 9, 10 or less mismatches. In some embodiments, the complementary sequence comprises 1%, 2%, 3%, 4%, 5%, 6%, 7%, 8%, 9%, or 10% or less mismatches.

"Percent (%) sequence identity" with respect to a reference sequence (subject) is determined as the percentage of amino acid residues or nucleotides in a candidate sequence (query) that are identical with the respective amino acid residues or nucleotides in the reference sequence, after aligning the sequences and introducing gaps, if necessary, to achieve the maximum percent sequence identity, and not considering any amino acid conservative substitutions as part of the sequence identity. Alignment for purposes of determining percent sequence identity can be achieved in various ways that are within the skill in the art, for instance, using publicly available computer software such as BLAST, BLAST-2. Those skilled in the art can determine appropriate parameters for aligning sequences, including any algorithms needed to achieve maximal alignment over the full length of the sequences being compared. The percent identity between the two sequences is a function of the number of identical positions shared by the sequences (e.g., percent identity of query sequence=number of identical positions between query and subject sequences/total number of positions of query sequence×100). For example, Clustal W method of aligning multiple sequences is described in Thompson J, Higgins D and Gibson T (1994). Clustal W: improving the sensitivity of progressive multiple sequence alignment through sequence weighting." Nucleic Acids Research, Vol 22: pp. 4673-80. Another method is Clustal V, described in Higgins D G and Sharp P M (1989). "Fast and sensitive multiple sequence alignments on a microcomputer." CABIOS, Vol. 5, No. 2: pp. 151-153.

Regarding the amplification of a target nucleic acid sequence (e.g., by PCR) using a particular amplification primer pair, stringent conditions permit the primer pair to hybridize only to the target nucleic-acid sequence to which a primer having the corresponding wild-type sequence (or its complement) would bind to produce a unique amplification product, the amplicon, in a DNA thermal amplification reaction.

The term "allele" refers to an alternative form of a gene, whereby two genes can differ in DNA sequences. Such differences may result from at least one mutation (e.g., deletion, insertion, and/or substitution) in the nucleic acid sequence. Alleles may result in modified mRNAs or polypeptides whose structure or function may or may not be modified. Any given gene may have none, one, or many allelic forms. Each of these types of changes may occur alone, or in combination with the others, one or more times in a given sequence.

A hybridization reaction using a probe specific to a sequence found within the amplicon is yet another method used to detect the amplicon produced by a PCR reaction. The term "zygosity" generally refers to the similarity of alleles for a gene or trait in an organism (e.g., a plant). If both alleles are the same, the organism is homozygous for the allele. If the two alleles are different, the organism is heterozygous for the gene or trait. If one allele is not present, the organism is hemizygous. If both alleles are not present, the organism is nullizygous. For example, a plant is homozygous for the trait of interest if the insert DNA along with the junction sequence is present at the same location on each chromosome of a chromosome pair (both the alleles). For example, a maize plant having Event DP-202216-6 at the same location on both the copies of the chromosome. Similarly, a plant is considered heterozygous if the transgene insert along with the junction sequence (e.g., Event DP-202216-6) is present on only one of the chromosomes of a chromosome pair (only one allele). A wild-type plant is considered "null" when compared to the transgenic Event DNA.

The term "label" when used herein refers to a detectable compound or composition that is conjugated directly or indirectly to a probe to generate a "labeled" probe. The label may be detectable by itself (e.g. radioisotope labels or fluorescent labels) or, in the case of an enzymatic label, may catalyze chemical alteration of a substrate compound or composition that is detectable (e.g., avidin-biotin).

As used herein, a "line" is a group of plants that display little or no genetic variation between individuals for at least one trait. Such lines may be created by several generations of self-pollination and selection, or vegetative propagation from a single parent using tissue or cell culture techniques.

As used herein, the terms "cultivar" and "variety" are synonymous and refer to a line which is used for commercial production. "Stability" or "stable" means that with respect to the given component, the component is maintained from generation to generation and, for some embodiments, at least three generations at substantially the same level, e.g., for some embodiments ±15%, for some embodiments ±10%, most for some embodiments ±5%. The stability may be affected by temperature, location, stress and the time of planting.

"Agronomically elite" means that a line has desirable agronomic characteristics such as maturity, disease resistance, standability, ear height, plant height, and the like, in addition to yield increase due to the subject event(s).

In some embodiments the DP-202216-6 maize event may further comprise a stack of additional traits. Plants comprising stacks of polynucleotide sequences can be obtained by either or both of traditional breeding methods or through genetic engineering methods. These methods include, but are not limited to, breeding individual lines each comprising a polynucleotide of interest, transforming a transgenic plant comprising a gene disclosed herein with a subsequent gene and co-transformation of genes into a single plant cell. As used herein, the term "stacked" includes having the multiple traits present in the same plant (i.e., both traits are incorporated into the nuclear genome, one trait is incorporated into the nuclear genome and one trait is incorporated into the genome of a plastid or both traits are incorporated into the genome of a plastid). Additional traits can include for example, drought tolerance and other abiotic stress tolerance traits. Such traits can be introduced by breeding with maize plants containing other recombinant events or with maize plants containing native variations or genome edited variations.

In some embodiments, DP-202216-6 maize event can be stacked with one or more additional input traits (e.g., herbicide resistance, fungal resistance, virus resistance, stress tolerance, disease resistance, male sterility, stalk strength, and the like) or output traits (e.g., increased yield, modified starches, improved oil profile, balanced amino acids, high lysine or methionine, increased digestibility, improved fiber quality, drought resistance, and the like). In a further embodiment, the DP-202216-6 maize event may be combined with one or more additional Bt insecticidal toxins or other non-Bt insecticidal proteins.

In an aspect, a corn field has plants that have the MAD S-box transcription factor disclosed herein along with introduced genetic modifications affecting stature, and includes a planting density of at least 10,000 corn plants per acre. In another aspect, a corn field comprises a planting density of at least 30,000 corn plants per acre. In another aspect, a corn field includes a planting density of at least 32,000 corn plants per acre. In another aspect, a corn field includes a planting density of at least 34,000 corn plants per acre. In another aspect, a corn field includes a planting density of at least 36,000 corn plants per acre. In another aspect, a corn field includes a planting density of at least 38,000 corn plants per acre. In another aspect, a corn field includes a planting density of at least 40,000 corn plants per acre. In another aspect, a corn field includes a planting density of at least 42,000 corn plants per acre. In another aspect, a corn field includes a planting density of at least 44,000 corn plants per acre. In another aspect, a corn field includes a planting density of at least 46,000 corn plants per acre. In another aspect, a corn field includes a planting density of at least 48,000 corn plants per acre. In another aspect, a corn field includes a planting density of at least 50,000 corn plants per acre. In another aspect, a corn field includes a planting density of at least 52,000 corn plants per acre. In another aspect, a corn field includes a planting density of at least 54,000 corn plants per acre. In another aspect, a corn field includes a planting density of at least 56,000 corn plants per acre. In another aspect, a corn field includes a planting density of at least 58,000 corn plants per acre. In another aspect, a corn field includes a planting density of at least 60,000 corn plants per acre.

In an aspect, a corn field has plants that have the MADS-box transcription factor, the corn plants containing MADS-box transcription factor expressing at a higher level in combination with shorter stature or semi-dwarf phenotype exhibits plant that is at least about 10%, between 10% and 15%, at least about 15%, between 15% and 20%, at least about 20%, between 20% and 25%, at least about 25%, between 25% and 30%, at least about 30%, between 30% and 35%, at least about 35%, between 35% and 40%, at least about 40%, between 40% and 45%, at least about 45%, between 45% and 50%, at least about 50%, between 50% and 55%, at least about 55%, between 55% and 60%, at least about 60%, between 60% and 65%, at least about 65%, between 65% and 70%, at least about 70%, between 70% and 75%, at least about 75%, between 75% and 80%, when compared to the plant height of control corn plants not comprising the stature genetic modification, when measured at or near reproductive/late reproductive growth phase (e.g., R1-R6).

In an aspect, a corn field has plants that have the MADS-box transcription factor disclosed herein along with introduced genetic modifications affecting stature and includes a planting density of between 10,000 and 50,000 corn plants per acre. In an aspect, a corn field includes a planting density of between 10,000 and 40,000 corn plants per acre. In an aspect, a corn field includes a planting density of between 10,000 and 30,000 corn plants per acre. In an aspect, a corn field includes a planting density of between 10,000 and 25,000 corn plants per acre. In an aspect, a corn field includes a planting density of between 10,000 and 20,000 corn plants per acre. In an aspect, a corn field includes a planting density of between 20,000 corn plants and 60,000 corn plants per acre. In an aspect, a corn field includes a planting density of between 20,000 corn plants and 58,000 corn plants per acre. In an aspect, a corn field includes a planting density of between 20,000 corn plants and 55,000 corn plants per acre. In an aspect, a corn field includes a planting density of between 20,000 corn plants and 50,000 corn plants per acre. In an aspect, a corn field includes a planting density of between 20,000 corn plants and 45,000 corn plants per acre. In an aspect, a corn field includes a planting density of between 20,000 corn plants and 42,000 corn plants per acre. In an aspect, a corn field includes a planting density of between 20,000 corn plants and 40,000 corn plants per acre. In an aspect, a corn field includes a planting density of between 20,000 corn plants and 38,000 corn plants per acre. In an aspect, a corn field includes a planting density of between 20,000 corn plants and 36,000 corn plants per acre. In an aspect, a corn field includes a planting density of between 20,000 corn plants and 34,000 corn plants per acre. In an aspect, a corn field includes a planting density of between 20,000 corn plants and 32,000 corn plants per acre. In an aspect, a corn field includes a planting density of between 20,000 corn plants and 30,000 corn plants per acre. In an aspect, a corn field includes a planting density of between 24,000 corn plants and 58,000 corn plants per acre. In an aspect, a corn field includes a planting density of between 38,000 corn plants and 60,000 corn plants per acre. In an aspect, a corn field includes a planting density of between 38,000 corn plants and 50,000 corn plants per acre.

In some embodiments, corn plants containing DP-202216-6 event can be crossed with corn plants containing other corn Events or combination thereof and the resulting properties of the progeny plants are evaluated. For example, corn plants containing DP-202216-6 Event can be crossed or combined with corn plants including one or more combinations, of the following: MON810; DAS-59122-7; MIR604; MON89034; MON863; MON87411; MON87403; MON87427; MON-00603-6 (NK603); MON-87460-4; MON-88017-3; LY038; TC1507; 5307; DAS-06275-8; BT176; BT11; MIR162; GA21; MZDT09Y; SYN-05307-1; DP-004114-3; and DAS-40278-9.

The following examples are offered by way of illustration and not by way of limitation. As described herein, Event DP-202216-6 is also referred to as "Event 16", "E16" "event 16" or "Event 16-6" and they all refer to the same maize event DP-202216-6. The protein encoded by the Maize MADS box ZmM28 gene in the plasmid PHP40099 or the Event DP-202216-6 is also referred to as AG099 protein and the corresponding DNA sequence as AG099 gene or AG099 DNA.

EXAMPLES

Example 1

Field Performance of Reduced Stature Maize Plants Having Increased and Extended Expression of AG099

A series of grain yield trials are conducted in elite corn hybrids across testing locations in order to assess the yield in elite reduced stature maize hybrids and reduced stature maize hybrids having AG099 events. For example, hybrids with maturities ranging from 105-112 days are used to evaluate the performance of reduced stature AG099 events relative to controls. In certain aspects, locations selected to achieve various yield levels can range from highly drought stressed 70 bu/acre to optimal growing conditions 250 bu/acre. Soil types include a variety of high sand, sandy loam, silty loam, loam and some clay. In such locations, entries containing the AG099 construct are compared to its control (e.g., AG099 alone or reduced stature plants alone, but not the combination) for each specific hybrid background. Two to four replicates of a split plot design are established at each location. A mixed model analysis of variance can be conducted using ASREML where BLUEs (Best Linear Unbiased Estimates) are generated for each AG099 event in combination with reduced stature or height lines and respective controls across hybrids within a given location. Pairwise contrasts of these event BLUEs to wild type BLUEs are analyzed to test significant differences.

In certain aspects, such as for example, high-yielding where yields of over 160 bu/acre are considered as normal and often can be greater than 180 bu/acre which represents a large portion of the most productive corn growing regions in the United States. In order to evaluate the response of reduced stature corn hybrids containing AG099 event or construct to drought stress, additional sites in Kansas, Texas and California can also be established with the capability of specifically managing the amount of water applied to the test plots during the growing season. Managed stress conditions can range from severe stress of less than 120 bu/acre yield up to a very mild stress where the yield is under 160 bu/acre.

Example 2

Field Performance of Reduced Stature Maize Plants Having Increased and Extended Expression of AG099 Under Varying Planting Densities and Row Spacing To test AG099 containing events with reduced stature and resulting yield increase under different planting populations, experiments are conducted at multiple locations and at varying planting population or planting density. Experimental treatments include planting populations of for example, 36,000, 40,000, 44,000, 48,000, 52,000, 56,000, 60,000, 70,000 or 75,000 plants per acre. Within each population, in certain experiments corn Event DP-202216-6 bred for reduced stature and the corresponding control (e.g., Event DP-202216-6 alone or the reduced stature line without the Event) are evaluated across multiple hybrid backgrounds. The grain yield of reduced stature corn having Event DP-202216-6 per acre within and across densities are measured by calculating the difference in yield (BLUEs) of the test line to that of the control.

To test AG099 containing events with reduced stature and resulting yield increase under different row width, experiments are conducted at multiple locations and at varying row width. Experimental seeding rates include planting densities of e.g., 36,000, 40,000, 44,000, 48,000, 52,000, 56,000, 60,000, 64,000, 65,000, 70,000 or 75,000 plants per acre at varying row width or row spacing. For example, row width can range from about 8 inches, 10 inches, 12 inches, 14 inches, 16 inches, 18 inches, 20 inches, 22 inches, 24 inches, 26 inches, 28 inches, 30 inches or other row widths that are available in mechanical planting equipment (seed planters). In addition, a twin row configuration, where two rows are e.g., 7-8" apart are also possible. Within each population, in certain experiments corn Event DP-202216-6 bred for reduced stature and the corresponding control (e.g., Event DP-202216-6 alone or the reduced stature line without the Event) are evaluated across multiple hybrid backgrounds. The grain yield of reduced stature corn having Event DP-202216-6 per acre within and across densities are measured by calculating the difference in yield (BLUEs) of the test line to that of the control.

TABLE 2

Predicted Field Yield and Plant Height for Short Stature Plants - Multilocation Field Trials Among Multiple Genetic Backgrounds

| Experimental Lines | % Yield Reduction Compared to Control | % Plant Height Reduction Compared to Control |
| --- | --- | --- |
| D8 short stature - Genetic Background 1 | 6.95 | 31.33 |
| D8 short stature - Genetic Background 2 | 9.56 | 33.98 |
| D8 short stature - Genetic Background 3 | 7.92 | 34.43 |
| D8 short stature - Genetic Background 4 | 8.53 | 30.64 |
| D8 short stature - Genetic Background 5 | 8.73 | 36.49 |

As part of the multilocation trials, in one of the locations, genetic backgrounds 4 and 5 for D8 had a statistically significant increase in yield compared to the NULL control (P<0.10 confidence).

Example 3

Secondary Trait Characteristics of Reduced Stature Maize Plants Containing Increased Expression of AG099 (e.g., Event DP-202216-6)—Inbred and Hybrid Analysis Secondary agronomic characteristics are observed for reduced stature maize plants that exhibit increased and extended expression of AG099. Agronomic parameters such as plant, ear height, early or late root lodging, brittle snap, grain moisture, anthesis-silking interval and others are measured. Growing degree units to silk (GDUSLK): Measurement records the total accumulated growing degree units when 50% of the plants in the plot have fully emerged silks. A single day equivalent is approximately 2.5 growing degrees units (GDU) for this data set. Growing degree units to shed (GDUSHD): Measurement records the total accumulated growing degree units when 50% of the plants in the plot have tassels that are shedding pollen. A single day equivalent is approximately 2.5 growing degrees units for this data set.

Ear height (EARHT): Measurement from the ground to the attachment point of the highest developed ear on the plant. Ear height is measured in inches.

Plant height (PLTHT): Measurement from the ground to the base of the flag leaf. Plant height is measured in inches.

Moisture (MST): Measurement of the percent grain moisture at harvest.

Yield: Recorded weight of grain harvested from each plot. Calculations of reported bu/acre yields are made by adjusting to measured moisture of each plot.

Agronomic data and observations are collected for the inbred trials and analyzed for comparison to a wild type entry (WT), or without the AG099 trait version of the same genotype or with respect to reduced stature, appropriate controls are used.

To evaluate the hybrid data, a mixed model framework is used to perform multi location analysis. In the multi-location analysis, main effect construct design is considered as fixed effect. Factors for location, background, tester, event, background by construct design, tester by construct design, tester by event, location by background, location by construct design, location by tester, location by background by construct design, location by tester by construct design, location by event, location by tester by event are considered as random effects. The spatial effects including range and plot within locations are considered as random effects to remove the extraneous spatial noise. The heterogeneous residual is assumed with autoregressive correlation as AR1*AR1 for each location. The estimate of construct design and prediction of event for each background are generated. The T-tests are conducted to compare construct design/event with WT. A difference is considered statistically significant if the P-value of the difference is less than 0.05. Yield analysis is by ASREML (VSN International Ltd; Best Linear Unbiased Prediction; Cullis, B. R et al (1998) *Biometrics* 54: 1-18, Gilmour, A. R. et al (2009); ASRem1 User Guide 3.0, Gilmour, A. R., et al (1995) *Biometrics* 51: 1440-50).

To evaluate the inbred data, a mixed model framework is used to perform multi location analysis. In the multi-location analysis, main effect construct design is considered as fixed effect. Factors for location, background, event, background by construct design, location by background, location by construct design, location by background by construct design, location by event and rep within location are considered as random effects. The spatial effects including range and plot within locations are considered as random effects to remove the extraneous spatial noise. The heterogeneous residual is assumed with autoregressive correlation as AR1*AR1 for each location. The estimate of construct design and prediction of event for each background are generated. The T-tests were conducted to compare construct design/event with WT. A difference is considered statistically significant if the P-value of the difference is less than 0.10. Yield analysis was by ASREML (VSN International Ltd; Best Linear Unbiased Prediction; Cullis, B. Ret al (1998) *Biometrics* 54: 1-18, Gilmour, A. R. et al (2009); ASRem1 User Guide 3.0, Gilmour, A. R., et al (1995) *Biometrics* 51: 1440-50).

to the NULL control (P<0.10 confidence). For yield the BLUE DIFF is bu/acre and for Ear height and Plant height the units are inches.

Experimental designs of the D8 experiments were split plots with hybrid background as the main plot and the D8*AG099 or D8 version of the hybrid as the sub plot. Two replicates were established at five testing locations with main plots randomized within replication and sub plots randomized within main plot. Experimental entries were grown in four-row plots that ranged from 4.4 m to 5.3 m in length with a 0.5 m alley in between. A mixed model analysis of variance was conducted using ASREML accounting for random field and spatial components as well as the fixed components. BLUEs were generated for both the D8*AG099 stacks and the D8 single entries across all hybrid backgrounds. Pairwise contrasts of the D8*AG099 and D8 single BLUEs conducted to test for significant differences (BLUE DIFFs) at P<0.10

Example 4

Nutrient Management of Reduced Stature AG099 Plants

Reduced stature maize AG099 expressing plants are grown at higher seeding rates. Further, such plants may exhibit early growth vigor and increased grain fill. Appropriate nutrient management considerations include:

Early and late season management practice for AG099 expressing short stature corn plants include for example,

TABLE 3

Field Standability Measurements for Plants Containing D8 Stature Genetic Modification Among Multiple Genetic Backgrounds

| Experimental Lines | % Difference in Standability Compared to Control Plants | | | | | |
|---|---|---|---|---|---|---|
| | Loc 1 | Loc 2 | Loc 3 | Loc 4 | Loc 5 | Loc 6 |
| D8 short stature - Genetic Background 1 | 40.68* | 19.25* | −0.83 | 22.64* | −1.84 | −8.95 |
| D8 short stature - Genetic Background 2 | 35.07* | −18.39 | 0.04 | 21.04* | −4.57 | −8.96 |
| D8 short stature - Genetic Background 3 | 38.69* | 20.61* | 0.69 | 25.38* | −0.94 | — |
| D8 short stature - Genetic Background 4 | 36.0* | — | −2.36 | 34.61* | −1.03 | — |
| D8 short stature - Genetic Background 5 | 44.07* | 15.17* | −1.05 | 15.99* | −1.90 | −8.96 |

As part of the multilocation trials, the data noted with an asterisk (*) denote statistically significant difference compared to the NULL control (P<0.10 confidence).

TABLE 4

Agronomic measurements for D8 in combination with AG099 from Multilocation Field Trials.

| Experimental Line | BLUE Difference Compared to D8 Single Control (Yield) | BLUE Difference Compared to D8 Single Control (Ear Height) | BLUE Difference Compared to D8 Single Control (Plant Height) |
|---|---|---|---|
| D8 + AG099 | 4.86 | 0.52 | −1.79 |

As part of the multilocation trials, in one of the locations, D8 had a statistically significant increase in yield compared reducing starter N and increasing side-dressing N application between V6 to V12, and delaying single application of N fertilizer and splitting N fertilizer applications at either the Agronomic Optimum N Rate (AONR) or the Economic Optimum N Rates (EONR). This management practice can also result in reduced overall Nitrogen application throughout the growing season per net yield of bu/acre. Over the top N application for shorter, but high-yielding AG099 plants are also contemplated. Maize plants expressing a recombinant maize polynucleotide sequence encoding the polypeptide (SEQ ID NO: 1) are field tested in combination with a height reduction phenotype.

Results can demonstrate that expression of the recombinant polynucleotide encoding SEQ ID NO: 1 in a reduced stature background can increase grain yield of maize under field conditions on a per unit of basis of applied nitrogen when compared to an appropriate control.

Example 5

Enhanced Disease & Pest Management of Reduced Stature AG099 Plants

Reduced stature maize AG099 expressing plants are grown at higher seeding rates than comparable corn hybrids. The occurrence of pests and diseases increases as plant density increases. Because short stature plants are planted at higher than normal densities, likelihood of plant diseases for short stature corn is high. In addition, under high-density planting, reduced stalk strength due to the possibility of lower cellulose and lignin content may increase corn borer infestation of stalks, which results in increased stalk lodging rate. Further, higher plant density generally corresponds to reduced spatial distance between individual maize plants. This spatial crowding or denser canopy adversely affects the ventilation and light conditions of maize canopies, which in turn can increase the spread of pathogens and of stalk rot spores. Since short stature plants have a denser canopy than taller/normal plants, planting at a high density may increase disease occurrence. In addition, absorption of nutrients at high planting density, is reduced. With shorter roots, semi-swarf plants may be under a higher pressure at high planting density, thereby limiting nutrient uptake. Reduced nutrient update can in turn decrease the soluble sugar content and physiological activity of stalk, thereby reducing the resistance of stalk to rot and sheath blight.

Further, such plants may exhibit early growth vigor and increased grain fill. Appropriate disease management considerations include:

- Seed treatment with fungicides and insecticides at a dosage rate that is different than conventional/control corn hybrids.
- Early and late season, such as reducing or increasing the amount and frequency of fungicides and insecticides applications.
- Planting the plants earlier than a normal planting schedule to enable the plants develop into a mature state earlier and resistant to disease infection before or during exposure to fungal spores. Alternatively, prescriptive pesticide application, over-the-top of semi-dwarf AG099 plants during mid or late season.

Maize plants expressing a recombinant maize polynucleotide sequence encoding the polypeptide (SEQ ID NO: 1) are field tested in combination with a height reduction phenotype, such as, for example genome edited Della (D8) variants that exhibit semi-dwarf phenotype.

Example 6

Gibberellic Acid Pathway Modification—Stature Reduction in Combination with Increased AG099 Expression Gibberellins have been identified as determinants of plant height in many plant species including maize and rice. Mutants such as sd1 in rice, rht-1 in wheat or barley sdw1 map to genes involved in gibberellin synthesis or signaling. Through CRISPR-Cas genome editing nucleic acid guided CAS endonucleases, mutations of GA pathway are introduced into more elite germplasm with minimal genetic drag associated with conventional breeding material. Through CRISPR-cas genome editing nucleic acid guided CAS endonucleases, weaker or stronger alleles of previously known mutations of GA pathway are introduced into more elite germplasm. Through CRISPR-cas genome editing nucleic acid guided CAS endonucleases, new variations of one or more components of the GA pathway are introduced into elite germplasm with minimal genetic drag associated with conventional breeding material. These targets include for example, GA1, GA3, GA4, GA7, GA20-oxidases (GA20ox), GA3-oxidases (GA3ox) and GA2-oxidases (GA2ox). Disruption of these enzymes through genome editing affects plant stature. GA20ox and GA3ox catalyze oxidations which convert inactive GAs into active GAs (GA20, GA1, GA4) and thus enhance GA responses. GA2ox deactivates GAs by converting GA4 and GA1 into inactive forms. Therefore, methods and compositions are provided that modulate the expression levels, activity levels and a combination thereof of GA these GA biosynthetic pathway that impact plant stature. More specifically, genome edited variants are provided that affect GA biosynthesis, GA signaling and/or a combination thereof.

Reduction in plant height through GA pathway manipulation along with increased and extended expression of AG099 results in overall increase in yield per acre of high-density corn.

Example 7

Genome Editing of DELLA Proteins and Other GA Regulators for Stature Modification in AG099 Maize Plants DELLA proteins are a subfamily of the GRAS superfamily of proteins and play an important role in the negative regulation of GA signaling. DELLA proteins such as D8, D9, and others are suitable targets for generating variations in protein function to alter stature. Through CRISPR-cas genome editing nucleic acid guided CAS endonucleases, mutations of DELLA proteins were introduced into more elite germplasm with minimal genetic drag associated with conventional breeding material. Through CRISPR-cas genome editing nucleic acid guided CAS endonucleases, weaker or stronger alleles mutations of DELLA proteins are introduced into more elite germplasm of plants such as maize, rice, wheat, sorghum and other crop plants.

TABLE 2

Agronomic characteristics of D8 genome edited plants.

| Hybrid | PHTYLD (bu/acre) | % Red'n | PHTKPE | % Red'n | Plant Height | % Red'n | Harvest Index | HI Difference |
|---|---|---|---|---|---|---|---|---|
| Hybrid 1 | 226 | 28 | 528 | 23 | 145 | 31 | 0.58 | 0 |
| NULL (Control 1) | 315 | | 681 | | 212 | | 0.58 | |

TABLE 2-continued Agronomic characteristics of D8 genome edited plants.

| Hybrid | PHTYLD (bu/acre) | % Red'n | PHTKPE | % Red'n | Plant Height | % Red'n | Harvest Index | HI Difference |
|---|---|---|---|---|---|---|---|---|
| Hybrid 2 | 191 | 35 | 504 | 28 | 143 | 34 | 0.58 | 0.03 |
| NULL (Control 2) | 292 | | 697 | | 217 | | 0.55 | |
| Hybrid 3 | 213 | 33 | 517 | 27 | 170 | 29 | 0.54 | 0.01 |
| NULL (Control 3) | 318 | | 704 | | 239 | | 0.53 | |
| Hybrid 4 | 197 | 37 | 500 | 29 | 153 | 36 | 0.54 | −0.01 |
| NULL (Control 4) | 312 | | 706 | | 237 | | 0.55 | |
| Across Hybrids | | 33 | | 27 | | 33 | | 0.0075 |

This table shows data collected from a field trial conducted in Johnston, Iowa. This replicated study included four elite Stiff stalk inbreds crossed to one genome edited non-stiff stalk D8 inbred, as well as their respective null comparators. In total, eight hybrids were tested. Traits that were taken at the end of the growing season and that are shown in the table are: 1) ear photometry estimated yield (PHTYLD), 2) ear photometry kernels per ear (PHTKPE), 3) Plant Height and 4) Harvest Index. For the ear photometry traits, multiple ears from each of two rows were harvested and analyzed with the standard Pioneer/Corteva ear photometry machine. Plant height was determined in the field using a measuring stick; while Harvest Index was measured as the difference in dry weight between all above ground vegetative tissue relative to the dry weight of the grain. Averaged across hybrids, the plant height of the D8 edited hybrids was reduced 33% relative to the nulls. Average estimated grain yield was also reduced in the edits by 33%, while the number of kernels per ear was decreased on average by 27%. Overall, there was minimal change in the Harvest Index.

In addition to DELLAs, feedback regulators of GA biosynthesis such as for example, RSG (Repression of Shoot Growth), a bZIP transcription factor, and its interactors 14-3-3, SCL3 (Scarecrow-like3), another member of the GRAS family and those components that have been identified as GA regulators are targets for genome editing. Therefore, methods and compositions are provided that modulate the expression levels, activity levels and a combination thereof of GA regulators such as DELLA that impact plant stature. More specifically, genome edited variants are provided that affect GA regulation, GA signaling and/or a combination thereof are provided herein.

Example 8

Brassinosteroid Pathway Modification in Combination with Increased AG099 Expressing Maize Lines Brassinosteroids are a group of steroid hormones that have been identified in many plant species for a variety of functions including stature. Brassinosteroid-deficient mutants have also been a significant source of dwarfism in crops such as barley, e.g., uzu-type barley, which is insensitive to brassinosteroid treatment, has lodging resistance and upright leaf angle; *Arabidopsis* BRI1; and rice D61, encoding the brassinosteroid receptor.

Through CRISPR-cas genome editing nucleic acid guided CAS endonucleases, previously known mutations of Brassinosteroid pathway are introduced into more elite germplasm with minimal genetic drag associated with conventional breeding material. Through CRISPR-cas genome editing nucleic acid guided CAS endonucleases, weaker or stronger alleles of previously known mutations of Brassinosteroid pathway are introduced into more elite germplasm of plants such as maize, rice, wheat, sorghum and other crop plants. Genome edited variants of Brassinosteroid pathway may exhibit varying degrees of one or more characteristics selected from: shortened upper internodes, shorter grain, upright leaves, delayed flowering time, delayed leaf senescence. In addition to the biosynthetic pathway, perception and signal transduction of the Brassinosteroid pathway are amenable to manipulation using the methods and compositions provided herein for modulating stature. Stronger or weaker alleles of BRI1, BRL1, BRL3 receptors are also suitable candidates for genome editing to improve stature, for example, by reducing plant height. Weaker alleles of the Brassinosteroid biosynthetic enzymes or targeting genes downstream of the major steps of the biosynthesis pathway may be helpful ways to address reducing plant height by modulating Brassinosteroid pathway, wherein the plant height reduction is not severe and semi-dwarf phenotype is obtained.

Reduction in plant height through Brassinosteroid pathway manipulation along with increased and extended expression of AG099 results in overall increase in yield per acre of high-density corn.

Example 9

Weaker Alleles of Br1 Mutation and Increased AG099 Expression

The candidate gene for br1 mutation mapped to c1_192.24cM with its physical location at 223,645,759-223,649,276 and there are 4 splice variants of the gene model listed in the database. Genotypic variation in 507 out of 600 analyzed maize lines (84%) at the br1 locus is covered by four haplotypes belonging to groups 1, 2, 4, and 6.

Weaker alleles of Br1 gene loci are generated by targeted mutagenesis of the Br1 genomic region and evaluating height reduction. Plants with moderate height reduction are bred with increase AG099 expressing plants.

Example 10

Mid/Late Season Application of Agriculturally Relevant Compositions Over AG099 Expressing Short Stature Field Corn Plants Higher yielding corn plants that exhibit reduced plant height are described. Specifically, AG099 corn plants (e.g., those that include heterologous expression of a MADS-box transcription factor such as Zmm28) that also exhibit shorter, dwarf, or semi-dwarf phenotype are described.

Application of crop inputs such as fertilizers, nutrient, fungicides, insecticide, herbicide, or other pesticides, or other applications such as applying pollen for increased seed production, cover crop seeds during growing season of corn, or other applications to corn fields during mid- or late season are described, where such application is possible over AG099 plants exhibiting dwarf, semi-dwarf or short stature that is about 10% shorter to about 50% shorter to a comparable normal height hybrid corn plant (e.g., height of about 2 meters during the growing season).

Short stature AG099 plants benefit from an extended application of crop inputs described above. For example, targeted application of herbicides to remove a particular type of weed in a late growing season can increase yield. This can be accomplished by a farm equipment that can pass through a late season corn field for over-the-top application without causing significant damage to the corn plants, especially when they are at later stages of vegetative/reproductive growth. Alternatively, an unmanned aerial vehicle, such as a drone, can also provided targeted application of a herbicide in a corn field at late season or mid-season, where the hybrid corn plants are at a height of greater than 1.5 meters, for example.

Another example where short stature AG099 plants benefit from an extended application of a crop input include for example, application of late-season nutrients. Given the high-yielding attribute of AG099 plants, shorter stature of AG099 plants provide an opportunity to apply late season fertilizer to replenish nitrogen resources, for example, during the reproductive phase.

Another example where short stature AG099 plants benefit from an extended application of a crop input include for example, application of mid/late-season fungicides. Mid/late-season diseases are better managed through a targeted application of one or more fungicides to minimize disease occurrence and/or disease symptoms.

Example 11

Root Growth Enhancement of AG099 Expressing Field Corn Plants that Also Exhibit Shorter Stature Shorter corn plants may also have shorter roots, thereby limiting their ability to grow deeper and acquire nutrients and water, among other components. While the reduced plant height may be advantageous for root lodging, for example due to environmental factors such as strong winds, planting density, the shorter roots may impact standability in certain soil types or soil conditions. Root lodging can occur during late vegetative stages and during later reproductive stages. In addition, root damage due to corn root worm pressure, drought conditions, soil compaction, fields where soil nitrogen has been lost due to wet condition and colder soil temperature during early season increase the likelihood of root lodging because the corn plants could not establish sufficient rooting.

To enhance root growth for corn plants having both a high yielding trait such as AG099 and a short stature phenotype, one or more agronomic practices are followed. For example, a root stimulant at planting or during the early season helps enhance root growth. Such a root stimulant can be seed applied (e.g., a seed treatment biological) or soil applied. In certain embodiments, additional genetic traits including QTLs, or transgenes, or genome edited variants that increase root growth are contemplated for combinations with short stature plants.

When corn plants exhibit poor standability (i.e., ability of a corn plant to stand upright to be harvested by standard farm equipment, such as a combine), harvestable yield may be lower than a field where standability is not significant. Dwarf corn plants, semi-dwarf corn plants, and or short stature corn plants, are better at resisting lodging. However, to further improve the performance and or to reduce higher % lodging or increase % standability, root growth enhancing agricultural compositions are provided for of high yielding short stature plants. Generally, "lodging" can refer to either stalk lodging or root lodging. Likelihood of stalk lodging for short stature corn plants is low.

Example 12

Hybrid Corn Seed Production Involving Female Inbred Corn Plants Exhibiting Shorter Stature and Higher Yield Due to the Heterologous Expression of MADS-Box Transcription Factor Higher yielding corn plants that are female inbred and that also exhibit reduced plant height are described. Specifically, AG099 corn plants (e.g., those that include heterologous expression of a MADS-box transcription factor such as Zmm28) that also exhibit shorter, dwarf, or semi-dwarf phenotype are described in a hybrid production setting. Seed production yield goes higher when the female parental inbred line in hybrid seed production yield higher. Female inbred lines containing an increased expression of a MADS box transcription factor that contributes to higher grain yield were also developed to exhibit shorter stature, for example up to about 10% to about 50% reduction in height compared to a typical or control female inbred corn plant.

In a seed production field, AG099 female inbred plants that exhibit a reduced plant height about 20% are planted in one row. In the adjacent row, male inbred plants exhibiting normal/typical plant height for a male inbred line are planted. The seed yield is determined by measuring the seed yield of the female plants in the field and normalized for an acre. Depending the environmental and growth conditions, higher corn seed yield is expected when the female inbred parental line is shorter relative to the male inbred parental line. Reduction in plant height for AG099 expressing plants enable improved pollen flow, thereby increasing fertilization, kernel set and seed yield. Overall seed yield in a seed production field where AG099 containing female inbred lines that are shorter compared to the male inbreds, is expected to be higher than a comparable field where the AG099 containing plants are of normal height and not shorter than the male inbreds.

What is claimed is:

1. A corn plant comprising a stature reducing genetic modification and a yield enhancing genetic modification, wherein the yield enhancing genetic modification comprises a heterologous regulatory polynucleotide operably linked to a polynucleotide that encodes a polypeptide comprising an amino acid sequence that is at least 99% identical to SEQ ID NO: 1 and wherein the corn plant exhibits a plant height reduction of about 5% to about 50% due to the introduced genetic modification at a genomic locus encoding a D8 polypeptide represented by SEQ ID NO: 6, when compared to a control corn plant not comprising the stature reducing genetic modification.

2. The corn plant of claim 1, wherein the plant comprises event DP-202216-6, wherein a representative sample of seed of said corn event has been deposited with American Type Culture Collection (ATCC) with Accession No. PTA-124653.

3. A seed produced from the corn plant of claim 1, wherein a progeny from the seed exhibits increased yield and reduced stature when compared to the control plant.

4. A method of increasing planting density of corn plants comprising a heterologous regulatory polynucleotide operably linked to a polynucleotide that encodes a polypeptide comprising an amino acid sequence that is at least 99% identical to SEQ ID NO: 1, the method comprising:
   a) providing corn plants wherein the expression of the polynucleotide encoding the polypeptide is increased when compared to a control plant;
   b) reducing plant height by introducing a genetic modification at a genomic locus encoding a D8 polypeptide represented by SEQ ID NO: 6 that results in reduced stature of the corn plants; and
   c) planting the corn plants at a planting density of about 30,000 to about 75,000 plants per acre.

5. The method of claim 4, wherein the corn plants comprise event DP-202216-6.

6. The method of claim 4, wherein the corn plants are planted in a plurality of rows having a row width of about 8 inches to about 30 inches.

7. The method of claim 4, wherein the corn plants yield an average of about 3 bu/acre compared to control corn plants.

8. A method of increasing nitrogen use efficiency of a population of corn plants per unit of applied nitrogen, the method comprising:
   a) providing the population of corn plants, wherein the expression of a polynucleotide that encodes a polypeptide comprising an amino acid sequence that is at least 99% identical to SEQ ID NO: 1 is increased due to a genetic modification compared to a control plant;
   b) modifying the plant height of the population of the corn plants by introducing a genetic modification at a genomic locus encoding a D8 polypeptide represented by SEQ ID NO: 6 that results in reduced stature of the population of the corn plants; and
   c) growing the population of plants in a crop growing environment where the applied nitrogen is about 10% to about 50% less than an application rate of about 100 lbs to about 400 lbs of nitrogen per acre.

9. The method of claim 8, wherein the corn plants comprise event DP-202216-6.

10. The method of claim 8, wherein the corn plants exhibit an increase in grain yield of an average of at least 3 bu/acre when compared to the control plant.

11. The method of claim 8, wherein the population of corn plants exhibit an increase in nitrogen use efficiency of at least about 5% when compared to the control plant.

12. The method of claim 8, wherein the nitrogen use efficiency is increased by applying late season nitrogen, wherein at least about 25% of total nitrogen applied is applied on or after V8-V12 stage.

* * * * *

SEQUENCE LISTING

<160> NUMBER OF SEQ ID NOS: 9

<210> SEQ ID NO 1
<211> LENGTH: 251

<212> TYPE: PRT
<213> ORGANISM: Zea mays

<400> SEQUENCE: 1

```
Met Gly Arg Gly Pro Val Gln Leu Arg Arg Ile Glu Asn Lys Ile Asn
1               5                   10                  15

Arg Gln Val Thr Phe Ser Lys Arg Arg Asn Gly Leu Leu Lys Lys Ala
            20                  25                  30

His Glu Ile Ser Val Leu Cys Asp Ala Glu Val Ala Leu Ile Val Phe
        35                  40                  45

Ser Thr Lys Gly Lys Leu Tyr Glu Tyr Ser Ser His Ser Ser Met Glu
    50                  55                  60

Gly Ile Leu Glu Arg Tyr Gln Arg Tyr Ser Phe Glu Glu Arg Ala Val
65                  70                  75                  80

Leu Asn Pro Ser Ile Glu Asp Gln Ala Asn Trp Gly Asp Glu Tyr Val
                85                  90                  95

Arg Leu Lys Ser Lys Leu Asp Ala Leu Gln Lys Ser Gln Arg Gln Leu
            100                 105                 110

Leu Gly Glu Gln Leu Ser Ser Leu Thr Ile Lys Glu Leu Gln Gln Leu
        115                 120                 125

Glu Gln Gln Leu Asp Ser Ser Leu Lys His Ile Arg Ser Arg Lys Asn
    130                 135                 140

Gln Leu Met Phe Asp Ser Ile Ser Ala Leu Gln Lys Lys Glu Lys Ala
145                 150                 155                 160

Leu Thr Asp Gln Asn Gly Val Leu Gln Lys Phe Met Glu Ala Glu Lys
                165                 170                 175

Glu Lys Asn Lys Ala Leu Met Asn Ala Gln Leu Arg Glu Gln Gln Asn
            180                 185                 190

Gly Ala Ser Thr Ser Ser Pro Ser Leu Ser Pro Ile Val Pro Asp
        195                 200                 205

Ser Met Pro Thr Leu Asn Ile Gly Pro Cys Gln His Arg Gly Ala Ala
    210                 215                 220

Glu Ser Glu Ser Glu Pro Ser Pro Ala Pro Ala Gln Ala Asn Arg Gly
225                 230                 235                 240

Asn Leu Pro Pro Trp Met Leu Arg Thr Val Lys
                245                 250
```

<210> SEQ ID NO 2
<211> LENGTH: 857
<212> TYPE: DNA
<213> ORGANISM: Zea mays

<400> SEQUENCE: 2

```
ccccatcacc attgctgcga cgagagtgag cgggagaggg taggtggcga ggcggcggag    60
atggggcggg ggccggtgca gctgcgccgg atcgagaaca agatcaaccg ccaggtgacc   120
ttctccaagc gccggaacgg gctgctgaag aaggcccacg agatctccgt gctctgcgac   180
gcagaggtcg cgctcatcgt cttctccact aaggggaagc tctacgagta ctctagccat   240
tccagcatgg aaggcattct tgagcgttac cagcgttact catttgaaga aagggcagta   300
cttaacccaa gtattgaaga ccaggcaaat tggggagatg aatatgtccg gttaaaatcc   360
aaacttgatg cacttcagaa gagtcaaagg cagctgttag agaacaattt gagttcactg   420
accataaaag aactccagca actggagcaa caactggaca gttctttgaa gcatattagg   480
tcaagaaaga atcagctcat gttcgattca atttccgcgc ttcagaaaaa ggagaaagca   540
```

| | |
|---|---|
| cttacagatc aaaacggtgt cctgcaaaag ttcatggagg cagagaagga gaaaaacaag | 600 |
| gctttgatga acgcgcagct ccgggagcag caaaatggag catcaacaag ctccccatca | 660 |
| ctttcaccac caatagttcc agattccatg ccaactctaa atatagggcc atgtcaacat | 720 |
| agaggggcag cagaatctga gtctgaaccg tctcctgctc ctgcacaagc aaacaggggc | 780 |
| aacctgccac catggatgct ccgcactgtc aagtaacagg tgaggtcttc ccagtgtagt | 840 |
| tttgcagctg atctcga | 857 |

<210> SEQ ID NO 3
<211> LENGTH: 1893
<212> TYPE: DNA
<213> ORGANISM: Zea mays

<400> SEQUENCE: 3

| | |
|---|---|
| atgaagcgcg agtaccaaga cgccggcggg agtggcggcg acatgggctc ctccaaggac | 60 |
| aagatgatgg cggcggcggc gggagcaggg aacaggagg aggaggacgt ggatgagctg | 120 |
| ctggccgcgc tcgggtacaa ggtgcgttcg tcggatatgg cggacgtcgc gcagaagctg | 180 |
| gagcagctcg agatggccat ggggatgggc ggcgtgggcg cgccggcgc taccgctgat | 240 |
| gacgggttcg tgtcgcacct cgccacggac accgtgcact acaatccctc cgacctgtcg | 300 |
| tcctgggtcg agagcatgct gtccgagctc aacgcgcccc agcgccgct cccgcccgcg | 360 |
| acgccggccc caaggctcgc gtccacatcg tccaccgtca aagtggcgc cgccgccggt | 420 |
| gctggctact cgatctcccc gcccgccgtg gactcgtcca gcagtaccta cgctctgaag | 480 |
| ccgatcccct cgccggtggc ggcgccgtcg gccgacccgt ccacggactc ggcgcgggag | 540 |
| cccaagcgga tgaggactgg cggcggcagc acgtcgtcct cctcttcctc gtcgtcatcc | 600 |
| atggatggcg gtcgcactag gagctccgtg gtcgaagctg cgccgccggc gacgcaagca | 660 |
| tccgcggcgg ccaacgggcc cgcggtgccg gtggtggtgg tggacacgca ggaggccggg | 720 |
| atccggctcg tgcacgcgct gctggcgtgc cggaggccg tgcagcagga gaacttctct | 780 |
| gcggcggagg cgctggtcaa gcagatcccc atgctggcct cgtcgcaggg cggtgccatg | 840 |
| cgcaaggtcg ccgcctactt cggcgaggcg cttgcccgcc gcgtgtatcg cttccgcccg | 900 |
| ccaccggaca gctccctcct cgacgccgcc ttcgccgacc tcttgcacgc gcacttctac | 960 |
| gagtcctgcc cctacctgaa gttcgcccac ttcaccgcga accaggccat cctcgaggcc | 1020 |
| ttcgccggct gccgccgcgt ccacgtcgtc gacttcggca tcaagcaggg gatgcagtgg | 1080 |
| ccggctcttc tccaggccct cgccctccgc cctggcggcc cccgtcgtt ccggctcacc | 1140 |
| ggcgtcgggc cgccgcagcc cgacgagacc gacgccttgc agcaggtggg ctggaaactt | 1200 |
| gcccagttcg cgcacaccat ccgcgtggac ttccagtacc gtggcctcgt cgcggccacg | 1260 |
| ctcgccgacc tggagccgtt catgctgcaa ccggagggcg atgacacgga tgacgagccc | 1320 |
| gaggtgatcg ccgtgaactc cgtgttcgag ctgcaccggc ttcttgcgca gcccggtgcc | 1380 |
| ctcgagaagg tcctgggcac ggtgcgcgcg gtgcggccga ggatcgtgac cgtggtcgag | 1440 |
| caggaggcca accacaactc cggcacgttc ctcgaccgct tcaccgagtc gctgcactac | 1500 |
| tactccacca tgttcgattc tctcgagggc gccggcgccg gctccggcca gtccaccgac | 1560 |
| gcctccccgg ccgcggccgg cggcacggac caggtcatgt cggaggtgta cctcggccgg | 1620 |
| cagatctgca acgtggtggc gtgcgagggc gcggagcgca cggagcgcca cgagacgctg | 1680 |
| ggccagtggc gcagccgcct cggcggctcc gggttcgcgc ccgtgcacct gggctccaat | 1740 |
| gcctacaagc aggcgagcac gctgctggcg ctcttcgccg gcggcgacgg gtacagggtg | 1800 |

| | |
|---|---|
| gaggagaagg acgggtgcct gaccctgggg tggcatacgc gcccgctcat cgccacctcg | 1860 |
| gcgtggcgcg tcgccgccgc cgccgctccg tga | 1893 |

<210> SEQ ID NO 4
<211> LENGTH: 2850
<212> TYPE: DNA
<213> ORGANISM: Zea mays

<400> SEQUENCE: 4

| | |
|---|---|
| cgcagctccc cacttctcat cgccccctt ttttaatttg tggccatctt tggggtggtg | 60 |
| ggcggaggat ttctaactgg atggtgaagt ttgtctggcg aaaaggacgg ctgcgacgaa | 120 |
| cccgtccatc gatccaacgc tgtgcgcgcg ttgggggagg gacctgccag gccccacctg | 180 |
| cagcgacaga ctattgatag atgccttcct ctctgatcac ctgatggctg atgccttcgc | 240 |
| ggccgtcttc gcctgccgct gctactacta gttgccttcc tcgcttcccc gtctcgcccc | 300 |
| agccgcttcc cccctcccct accctttcct tccccactcg cacttcccaa ccctggatcc | 360 |
| aaatcccaag ctatcccaga accgaaaccg aggcgcgcaa gccattatta gctggctagc | 420 |
| taggcctgta gctccgaaat catgaagcgc gagtaccaag acgccggcgg gagtggcggc | 480 |
| gacatgggct cctccaagga caagatgatg gcggcggcgg cgggagcagg ggaacaggag | 540 |
| gaggaggacg tggatgagct gctggccgcg ctcgggtaca aggtgcgttc gtcggatatg | 600 |
| gcggacgtcg cgcagaagct ggagcagctc gagatggcca tggggatggg cggcgtgggc | 660 |
| ggcgccggcg ctaccgctga tgacgggttc gtgtcgcacc tcgccacgga caccgtgcac | 720 |
| tacaatccct ccgacctgtc gtcctgggtc gagagcatgc tgtccgagct caacgcgccc | 780 |
| ccagcgccgc tcccgcccgc gacgccggcc ccaaggctcg cgtccacatc gtccaccgtc | 840 |
| acaagtggcg ccgccgccgg tgctggctac ttcgatctcc cgcccgccgt ggactcgtcc | 900 |
| agcagtacct acgctctgaa gccgatcccc tcgccggtgg cggcgccgtc ggccgacccg | 960 |
| tccacggact cggcgcggga gcccaagcgg atgaggactg gcggcggcag cacgtcgtcc | 1020 |
| tcctcttcct cgtcgtcatc catggatggc ggtcgcacta ggagctccgt ggtcgaagct | 1080 |
| gcgccgccgg cgacgcaagc atccgcgcg gccaacgggc ccgcggtgcc ggtggtggtg | 1140 |
| gtggacacgc aggaggccgg gatccggctc gtgcacgcgc tgctggcgtg cgcggaggcc | 1200 |
| gtgcagcagg agaacttctc tgcggcgag gcgctggtca agcagatccc catgctggcc | 1260 |
| tcgtcgcagg gcggtgccat gcgcaaggtc gccgcctact tcggcgaggc gcttgcccgc | 1320 |
| cgcgtgtatc gcttccgccc gccaccggac agctccctcc tcgacgccgc cttcgccgac | 1380 |
| ctcttgcacg cgcacttcta cgagtcctgc ccctacctga agttcgccca cttcaccgcg | 1440 |
| aaccaggcca tcctcgaggc cttcgccggc tgccgccgcg tccacgtcgt cgacttcggc | 1500 |
| atcaagcagg ggatgcagtg gccggctctt ctccaggccc tcgccctccg ccctggcggc | 1560 |
| cccccgtcgt tccggctcac cggcgtcggg ccgccgcagc ccgacgagac cgacgccttg | 1620 |
| cagcaggtgg gctggaaact tgcccagttc gcgcacacca tccgcgtgga cttccagtac | 1680 |
| cgtggcctcg tcgcggccac gctcgccgac ctggagccgt tcatgctgca accggagggc | 1740 |
| gatgacacgg atgacgagcc cgaggtgatc gccgtgaact ccgtgttcga gctgcaccgg | 1800 |
| cttcttgcgc agcccggtgc cctcgagaag gtcctgggca cggtgcgcgc ggtgcggccg | 1860 |
| aggatcgtga ccgtggtcga gcaggaggcc aaccacaact ccggcacgtt cctcgaccgc | 1920 |
| ttcaccgagt cgctgcacta ctactccacc atgttcgatt ctctcgaggg cgccggcgcc | 1980 |

```
ggctccggcc agtccaccga cgcctccccg gccgcggccg gcggcacgga ccaggtcatg    2040
tcggaggtgt acctcggccg gcagatctgc aacgtggtgg cgtgcgaggg cgcggagcgc    2100
acggagcgcc acgagacgct gggccagtgg cgcagccgcc tcggcggctc cgggttcgcg    2160
cccgtgcacc tgggctccaa tgcctacaag caggcgagca cgctgctggc gctcttcgcc    2220
ggcggcgacg ggtacagggt ggaggagaag gacgggtgcc tgaccctggg gtggcatacg    2280
cgcccgctca tcgccacctc ggcgtggcgc gtcgccgccg ccgccgctcc gtgatcaggg    2340
aggggtggtt ggggcttctg gacgccgatc aaggcacacg tacgtcccct ggcatggcgc    2400
accctccctc gagctcgccg gcacgggtga agctagacgt cattgagcgc tgaatcgcag    2460
ttagcgaccg ggccaaggtt ctcgccggcg tgatgagatg gaacactttg actcccgcgg    2520
ccggatcggc ctgtgttcgt tcttgtttcc gatctcccct tctctttccg ttgcttcgat    2580
cccgtcaagt atggtagacc gtagcctatt gttatgttta aatgtcaatt attatgtgta    2640
attcctccaa gcgccgatat ccaataagga cgaaccggat tttcgttagc tcgacctcga    2700
atgagaattt tgtatacaat gcatcctcgt tagctatgtt catctgttcg aatgcttgtg    2760
ccctcatgtt ttcattccgt tcgtcctcta cacgaatggt gatcactatg tattgtgaac    2820
gagctcagtc atgtaggagc tgccagattg                                    2850
```

<210> SEQ ID NO 5
<211> LENGTH: 8124
<212> TYPE: DNA
<213> ORGANISM: Zea mays

<400> SEQUENCE: 5

```
tacgaatcta gagattcgtc tacaatgatt tgaggacagg tgtgagtttt caaaagaaaa      60
tgctttcaaa aaagtatgat gaagggtttt caccottatc accttgagt agggatgatc      120 agggactccc tggtttaggg gagggcctaa ggtgatggat cagctggttt aggtgtgagc     180
agaaggattc ccctcaca taaggaccgg tttgtcatcc ttcactacct gtactcatga      240
taagtacaac cactcgagac tatgtgggca gtcactcaat ctgaactcgt acggtccaac     300
cctagggtta tgaaggttgg ggaacaccgg gaggataagg aggggaatg ttttgtccgg      360 tttggacatg gtggtggcct gactccttcc ggtataaccg ttaaggttag gatgtgcgag    420
gaaagaaaga gattcggcat tcgggtctca cgacggtgag atcgcagaaa tcggactagt    480
ggataaagtg tacatctctg cgcagagttt gaaaatctat tcgaatagtc cgtgtccaca    540
ggaatggtcg agtctggtat ggtatggcaa ttaatgtttt gttttcaaaa aagggtgcat   600
ttgagaaaaa tgtttttaaa aagtccgacg gttgagccgt gagctatggt ggacgggaag   660
tccagtagct gttttgaaa atgaaaacca gtgggaaact gctgagatac ctggatggtt    720
tagtccaggg gattttgttc tatattgaaa aacttcctgc tcctttggga gaggatgcgc    780
tttgcaaaat acaaaatgtt ttacaaaaca accccgcata aaatattgtt gtttctgcaa    840
aatatcctga gctccagata ttccatgcat tatatctgat ttccccattc gcgggtgaa     900 ggtgggctgc tgagtacgtt tgtactcacc cttgcttatt tgttgttttt cagaaaaagg    960
agatcgggta agagttacga ctgttcccaa ccttgcctgt ggttgttgga ccgctgaatt    1020
gcttcgatgc gtatatcggg ctgcttcagc cccactttga tgatatgtcc ctagttgtgg    1080
accaactctt aaagttgttc gccaccttta taggtttgta tcgtttaagc agatctgtaa    1140
tcatctgatg tataaatgtg tttactagcc tcctgggact agtaattgta tcacatttga    1200
gtcccagagg attggggcgc ttcattgtac atggcttgtg gctcctctcc ttggttgagg    1260
```

```
atgaattgac cgagctcccc ctcgatcgtc tcccgcttgg tgatcttggt cacctcatcc    1320
ccttcatgtg cgatctttag aacatcccaa atctctttgg cacttttcat cccttgcacc    1380
ttattatact cctctcgaca tagagaggcg aggagtatag tggtggcttg ggagtcaaaa    1440
tgccagattt gggcgacctc gtccgagtca tagccttcat cccccacaga tggtacctgc    1500
gctccaaact caacaatgtc ccaaatgcta gagtggagtg aggttagatg atgcctcatt    1560
ttatcactcc acatacaata atcttcaccg taaaaaaccg gtggtttgcc taatgggaca    1620
gaaagtaaag gagtgcgttt agaaatgcgg ggatagcgta ggggaatctt actaaacttc    1680
ttgcgctcat ggcgcttaga agtgacggac gacacgttgg agccgtaggt ggatgacgac    1740
gaagagtcag tctcgtagta gactaccttc ttcatcttct tcttttttgtc gccactccga    1800 tgcgacttga cgcgagaagg tgattcctcc cttcctttgg cgccagactc ctttgatgga    1860
gccttcccgc ggcttgtgtc tgtttccatc tccctcttag cggatcctcc cgacaccact    1920
ttgagtggtt agtctctaat gaagtatcgg gttctgatac caattgaaag tcgcctagag    1980
ggggtaaata ggcggaaact gaaatttaca aattttaggc acaactataa gccgaggtta    2040
gtgttagaaa taaaaccaag tccgaaagag agagcgaaaa caaatcaacc aagaaataag    2100
cgagtgacac ggtgatttgt tttaccgagg ttcggttctt gcaaacctac tccccgttga    2160
ggtggtcaca aagaccgggt ctctttcaac cctttccctc tttcaaacgg tcacctagac    2220
cgagtgagct tccttccttg atttcccgag tcacttagac cccgcaagga ccaccacaca    2280
attggtgtct cttgcttcgc ttacaaggct ttgagagtaa gaatgagaga aagaagaaag    2340
ccaaccaagc aacaagagca acaaaagaac acaagtcgat cttctcacaa gtcctaaaaa    2400
ctaagttgaa ttgtggactt tgatttgatc ggaggctttg atttgtgtct tggagtgttg    2460
tgtattgctc ttgtattgaa tgaggagtag tgaatgctta atcttgaat ggtggtggtt    2520 gggggtattt atagccccaa ccaccaaaac agccgttggg gagggttgct gtcgatgggc    2580
gcaccggaca gtccggttcg ccaccggaca ctgtccggtg cgccaaccac gtcacccaac    2640
cgttagggtt ctgacggttt cgaccattgg agctctgaca tcttggtgca ccggacagtc    2700
tggtgccgca ccgtacaggc attgtacact gtccggtgcg cctctggcgc ctgctctgac    2760
ttctgccgcg actgtagctt tgttagggca ctgtgcagtc gatcgttgcg ctgatagccg    2820
ttgctccgct tggtgcaccg acagtccgg tggcacaccg acagtcaag tgaattacag    2880 cggagtgcgc ctggagaaac ccgaaggtga agagtttgag gtcgatccac cctggtgcac    2940
cggacactgt ccggtgcgcc agaccagggt tctcttcggt ttcttttgct cctttctttt    3000
gaaccctaac tttaatcttt ttattggttt gtgttgaacc tttagcacct gtagaatata    3060
taatctagag caaactagtt agtccaatta tttgtgttgg gcatttcaac caccaaaatc    3120
atttaggaaa aggtttgacc ctatttccct ttcacgtatg taatcatttc aatatgaaat    3180
aatgaataac aaaatgggcc aatacaattt cattttgcca agttttatt accttttta    3240 accttgtccc attcatgaat cccctcttgg aagattaata aatgggtgaa agggaatatt    3300
ttatttgtgt tgccttgttt ttatatttt taggaataaa aaacaagtga ccaatattgg    3360
catccaccta cggtaaattc acaaccacaa cgaagagtgt ggcaagctgt gtagcttcat    3420
catcgggctc aaagaagctt gtcttcccca tcaccgggcg atcgatcata cttcgaacta    3480
aacaacaaaa gatagaagaa agaagtccaa agaaaggtac aacttgttgg tgttcaaggg    3540
ccctacatta gatctaagag gtctcatatt ccaatcacat tatctcgaga agaccttcag    3600
```

```
atcaaatatt acccacacaa agatgctatg gtaatcttgt atgtcataaa agacttcgta    3660
gtccgcaatg tcttggtcga cacaggcagt gcagtcgata tcatctttac gaaagcgttc    3720
aaactgtaga aaacagtgat gcctaagaga gggatgaatt aggacatcta aaaactatgt    3780
ctaaacaagg ccacaattaa atctctagag caaagcctat gcaaaaaaaa caatctagaa    3840
tgtgcaaact aggttttgtc taagtgtcgc tatctctatt gcaaagtcta agtttcaatc    3900
ataaataatc taactagaaa ggcgaggttg aaacttacat acttaatata aatacggaag    3960
gtaaagagta aggtagatat gcaaactctc gtggatgacg ccagtatttt tattgaggta    4020
tctgaaacca cgcaaaggtt ccgactaatc ctcgttggtg cccctacgca aatggtagcc    4080
cacacgaggt ccaagcacct cggtcaagta actccgtaga gagccacatg ccttctccac    4140
gcgcaagtgg tgctctgctt tcggctcctc tcggacgctc cccgacgtct ccactatcga    4200
gcttccagct gaaatatcgt gggcctcgtt ccctccggta cactatggcg accgtgacac    4260
aaactcggtt gtcacgatct tgcaagacta tcgccccact tgatacaatt acaacgactc    4320
gcacaagagc tgaggggttg tgtgattttt ctaaacccac ccaactaact aggattcacc    4380
aagagcaagc gcataagtgg tctaactaac ttaagcactt cgcgaagaac ctacgctaat    4440
cactgagtga ttctattaag caatagggtg tttgagcact tggattgtct acaatatgcc    4500
ttgatatgtt gcttaggctc ccacaccttc aaatggccgg ttttgggggt atttataggc    4560
ttcccctca attatagcca tcagacagaa agctgttatt tctgtcgacg ggcgcaacgg    4620
acatgcattg ttcactgtcc agtgccatag ccacgtcagt cgaccgttag ggtctgtagc    4680
agtcgaccgt tggatccgac cattaactag actgtttggt gcacaccgga tagtctcgtg    4740
ctacaaccaa gagcgcttgg ttgtgggcct cacagcgcat actgcccggt gtcccaccgg    4800
acaggtactg cttgtctggt ccgccaccag tgcgctggct gactacccac tttatggatt    4860
tctttgttgt ttccttgggc ttcttttgtt cttgagtctt ggacttctac gtttctttta    4920
tgccttcttt tgaggtgttg catccgtagt gccttagtcc aatcctcttc gcatcctgtg    4980
gactataaat acaaacacta gaacataagt tgctttcgat atcattgata tggagttccc    5040
atacaacgca atcattggaa gaggagcact taatcctttc aaagtagtcc tagatttagc    5100
ttatatttgt atgaagatat caagcaagta ggacattata tcagcatata aaagccaaga    5160
agccacgaga agggtcgaag gaacctggca agaatacaag gccatccata atactgatta    5220
aaccgaagat caagcacaag acaaacaagt taaacaaaaa tagttttggc agattagccg    5280
aagtaaattc tcctctgtga agatgtggcc gaccaaaggg ttttgttcgg ttcacaatca    5340
acctcagaac aagagacatg ccttaaaaga ttcatgttta acaacaatca tgtcttcgct    5400
tggtgagcca acaatctatg tgggtttgat aggagcatca tagagcatgc actcaatgtt    5460
gatccaagta ttaaaccaag aaagcaaaag cttcgaaaga tgtccaatga taagaccgac    5520
gttaaaaggc tccttggtgc tagagtaata agagaagttg cctacctaga atggcttgct    5580
aacacatgca tggttaagaa accaaatgga aaatggagga tgtgcattga tttcacagat    5640
cttaacaaaa cttgcccgaa tgataaattc cccttcccag ggattaactc ccttgtatat    5700
gtagcataca cttcggagct catgagcttt ctagattgtt attcaaggta tcatcaaatt    5760
tggatgagaa aagaagacga accaaagacc aacttcataa cccctagtag aacttattat    5820
taccctttgga tgcctaaaga gctgaagaat gctggtggaa cgttcaacag aatgacagac    5880
aaagtcctca acacacaaat tgggagaaat gtactaacat atgtggatga tatcattgtt    5940
agaagcacaa gacaagaaga ccaaaattca tatttacaag aaacctttgt caacttctga    6000
```

```
aaagctggta tgaagtttaa tcccgagaaa tgtgttttcg tggtgaaggg gaaattcttt    6060
ggctgcctca tgtcgaccaa aggaattgaa gcaaacccccc acaacataga agctatccta   6120
tgaatggagc taccgaagtc aagaaaaggg gctcagctgt tggtaggcag acatgcttcc    6180
ttgaatagat tcatctcaat atctgcataa tgaagcttgc tattctttga agtgctaaag    6240
tcagctgaag tatttcaatg gggaccactc aacatcaagc cttcaaaggg tttaagcagc    6300
atctaattca cttgacaact ctcgtgcttt tcatgcgta aaatataaag gagaggttct      6360
tgggatcggt tacgcttatt gctttctcat gctccagcct ccgtctttcc tttccctagg    6420
agcttttctg ccgtcgcgcc tccttgctcg tgtgtccgtc ctgcttgctc ctcgcgccca    6480
tggcctcctt cccatcctgc tcaattcgta gagctacctt cttggtctag agaagatggg    6540
gttcatcccc ttaacgaagg tctcggggtg gagattggaa aatgagggtg aggtgttgta    6600
tccaagggac gacgaggtgt cgtgcttgcg tcctgctaca agcatgggtt tggcctgccc    6660
cttcgtccct tcgtatgggg gatactccac tactattagc tggagatcca gaatctccac    6720
cccaacaccg tcctccatat agcgtgtttt attacgctat atgaggcttt tatgggcatc    6780
gatccctatt ggaagttgtg gcagtatctc tttagcgcgt gggtgacttt gggtcgtggc    6840
ggtcaatcgt ttggtggctc agcctccatc caactcctct ctagctggaa ggcagagtat    6900
ttcaagatct tgcttccctc catcattcgg tacgagggtg agtggttcta cgccaagaat    6960
ctgcccggca gtgctgtacc gtacatcgga tgggagccgc tttcgacgaa taagtggcac    7020
catggcacgg atgcacgttc caagagctaa gtggagcagc ttctaaaggc gatcaccacg    7080
ttgaagcagc acggtcttac cagcgtgtgg cttatgcgtg tttttaatgca acgccgggtt    7140 aagcctcaga tggcctgcta aaacccgttg tacaagtact ctagcgtcga caaccccggc    7200
cgccattcct ccaagcctct tgcgctgacc gagatcgaga ctgcgggtct aggctatcac    7260
cgttctattg ttgtgggcct ttatggacga gaatttgcct cacccacttt ccaaagttgt    7320
tctgatatgc tttgtggtag gtatatctat ttatcctctt ttcatgttat caaattacat    7380
atcaaatctc atcctccaca ggctcaccag tcaccaacat caatcgttct ttgtgaaacc    7440
ctgtgctgga atacacacgc tcaatacatt agttggtaca tgagtctaat gaagtcaggg    7500
aaagagtact aattttcgcg agtaaaggga aggctggatc cttttttagtt gcattgatct    7560 tggcttggta gtcctcccca ctcgcgacat ctctctagcc gcacgctgga ctacagagtt    7620
agttccgcaa gctataaaat tcggctcgcc attggcttgc aagattgagt agtgagccgt    7680
ggacgcagct ccccacttct catcgccccc ttttttttaat ttgtggccat ctttggggtg    7740
gtgggcggag gatttctaac tggatggtga agtttgtctg gcgaaaagga cggctgcgac    7800
gaacccgtcc atcgatccaa cgctgtgcgc gcgttggggg agggacctgc caggccccac    7860
ctgcagcgac agactattga tagatgcctt cctctctgat cacctgatgg ctgatgcctt    7920
cgcggccgtt ttcgcctgcc gctgctacta ctagttgcct tcctcgcttc ccgtctcgc    7980 cccagccgct tcccccctcc cctacccttt ccttcccccac tcgcacttcc caaccctgga   8040
tccaaatccc aagctatccc agaaccgaaa ccgaggcgcg caagccatta ttagctggct    8100
agctaggcct gtagctccga aatc                                             8124
```

<210> SEQ ID NO 6
<211> LENGTH: 630
<212> TYPE: PRT
<213> ORGANISM: Zea mays

```
<400> SEQUENCE: 6

Met Lys Arg Glu Tyr Gln Asp Ala Gly Gly Ser Gly Gly Asp Met Gly
1               5                   10                  15

Ser Ser Lys Asp Lys Met Met Ala Ala Ala Gly Ala Gly Glu Gln
            20                  25                  30

Glu Glu Glu Asp Val Asp Glu Leu Leu Ala Ala Leu Gly Tyr Lys Val
                35                  40                  45

Arg Ser Ser Asp Met Ala Asp Val Ala Gln Lys Leu Glu Gln Leu Glu
        50                  55                  60

Met Ala Met Gly Met Gly Val Gly Gly Ala Gly Thr Ala Asp
65                  70                  75              80

Asp Gly Phe Val Ser His Leu Ala Thr Asp Thr Val His Tyr Asn Pro
                    85                  90                  95

Ser Asp Leu Ser Ser Trp Val Glu Ser Met Leu Ser Glu Leu Asn Ala
                100                 105                 110

Pro Pro Ala Pro Leu Pro Pro Ala Thr Pro Ala Pro Arg Leu Ala Ser
            115                 120                 125

Thr Ser Ser Thr Val Thr Ser Gly Ala Ala Gly Ala Gly Tyr Phe
130                 135                 140

Asp Leu Pro Pro Ala Val Asp Ser Ser Ser Thr Tyr Ala Leu Lys
145                 150                 155                 160

Pro Ile Pro Ser Pro Val Ala Ala Pro Ser Ala Asp Pro Ser Thr Asp
                165                 170                 175

Ser Ala Arg Glu Pro Lys Arg Met Arg Thr Gly Gly Ser Thr Ser
            180                 185                 190

Ser Ser Ser Ser Ser Ser Ser Met Asp Gly Gly Arg Thr Arg Ser
        195                 200                 205

Ser Val Val Glu Ala Ala Pro Pro Ala Thr Gln Ala Ser Ala Ala Ala
        210                 215                 220

Asn Gly Pro Ala Val Pro Val Val Val Asp Thr Gln Glu Ala Gly
225                 230                 235                 240

Ile Arg Leu Val His Ala Leu Leu Ala Cys Ala Glu Ala Val Gln Gln
                245                 250                 255

Glu Asn Phe Ser Ala Ala Glu Ala Leu Val Lys Gln Ile Pro Met Leu
                260                 265                 270

Ala Ser Ser Gln Gly Gly Ala Met Arg Lys Val Ala Ala Tyr Phe Gly
            275                 280                 285

Glu Ala Leu Ala Arg Arg Val Tyr Arg Phe Arg Pro Pro Pro Asp Ser
        290                 295                 300

Ser Leu Leu Asp Ala Ala Phe Ala Asp Leu Leu His Ala His Phe Tyr
305                 310                 315                 320

Glu Ser Cys Pro Tyr Leu Lys Phe Ala His Phe Thr Ala Asn Gln Ala
                325                 330                 335

Ile Leu Glu Ala Phe Ala Gly Cys Arg Arg Val His Val Val Asp Phe
                340                 345                 350

Gly Ile Lys Gln Gly Met Gln Trp Pro Ala Leu Leu Gln Ala Leu Ala
        355                 360                 365

Leu Arg Pro Gly Gly Pro Pro Ser Phe Arg Leu Thr Gly Val Gly Pro
    370                 375                 380

Pro Gln Pro Asp Glu Thr Asp Ala Leu Gln Gln Val Gly Trp Lys Leu
385                 390                 395                 400

Ala Gln Phe Ala His Thr Ile Arg Val Asp Phe Gln Tyr Arg Gly Leu
                405                 410                 415
```

Val Ala Ala Thr Leu Ala Asp Leu Glu Pro Phe Met Leu Gln Pro Glu
                420                 425                 430

Gly Asp Asp Thr Asp Asp Glu Pro Glu Val Ile Ala Val Asn Ser Val
            435                 440                 445

Phe Glu Leu His Arg Leu Leu Ala Gln Pro Gly Ala Leu Glu Lys Val
    450                 455                 460

Leu Gly Thr Val Arg Ala Val Arg Pro Arg Ile Val Thr Val Val Glu
465                 470                 475                 480

Gln Glu Ala Asn His Asn Ser Gly Thr Phe Leu Asp Arg Phe Thr Glu
                485                 490                 495

Ser Leu His Tyr Tyr Ser Thr Met Phe Asp Ser Leu Glu Gly Ala Gly
            500                 505                 510

Ala Gly Ser Gly Gln Ser Thr Asp Ala Ser Pro Ala Ala Gly Gly
    515                 520                 525

Thr Asp Gln Val Met Ser Glu Val Tyr Leu Gly Arg Gln Ile Cys Asn
    530                 535                 540

Val Val Ala Cys Glu Gly Ala Glu Arg Thr Glu Arg His Glu Thr Leu
545                 550                 555                 560

Gly Gln Trp Arg Ser Arg Leu Gly Gly Ser Gly Phe Ala Pro Val His
                565                 570                 575

Leu Gly Ser Asn Ala Tyr Lys Gln Ala Ser Thr Leu Leu Ala Leu Phe
            580                 585                 590

Ala Gly Gly Asp Gly Tyr Arg Val Glu Glu Lys Asp Gly Cys Leu Thr
    595                 600                 605

Leu Gly Trp His Thr Arg Pro Leu Ile Ala Thr Ser Ala Trp Arg Val
    610                 615                 620

Ala Ala Ala Ala Ala Pro
625                 630

<210> SEQ ID NO 7
<211> LENGTH: 1149
<212> TYPE: DNA
<213> ORGANISM: Zea mays

<400> SEQUENCE: 7
atgccgtgct cgtcgccggc cccgacatgg ctgctgcgag tgtcgccagc ggctgccgcg      60
gccgaccagg ccgccgcctc gtcctcgtgc tcatccaagg gcggaggccg cgtgctcacg     120
gccggtacca ccaccatgga cacggccgcc accgctgccg ccggcggcaa tgccgccgac     180
ctccaggaga gcagcagcag cggccagtcc cggctcgcgg cgcgcggcca ctggcgccca     240
gcggaggacg ccaagctccg tgagctcgtc gcgctgtacg gccccagaa ctggaacctc     300
atcgccgaga agctggacgg cagatccggg aagagctgcc gcctccgctg gttcaaccag     360
ctagaccccc ggatcagcaa gcgccccttc agcgacgagg aggaggagcg cctgatggct     420
gcgcaccgct tctacggcaa caagtgggcc atgatcgcgc cctcttccc cggccgcacg     480
gacaacgccg tgaagaacca ctggcacgtc atcatggcgc gcaagtaccg cgagcagtcc     540
acggcctacc gccgccgcaa gctcaaccag gcagtccagc ggaagctcga ggcagcctcc     600
gccgcggtcg caatgccgcc gggcgcgggc gcggagacg tcgccgtcgg ccagcaccac     660
cacctgctgg ccgccgccgc ggcggcccac gccacgacg ccgcctacag cttcgccgcg     720
gaccctacg gcttcggcat ccgccaccaa tactgcacct tcccgttccc gccaggcgcc     780
gcttcggctg aggacccgcc gccgccaacg caaatacatc ccttctgctt gttccctggg     840

| | |
|---|---|
| cccagcagcg cggcggcgca cgccgacagc aggcgccttc cctggccgcc gtcgtcggac | 900 |
| gcgcccggcg tcgcccggta cggggagccg catcagctcc tgcagctgcc cgttcaaagc | 960 |
| ggctggatcg acggcgtcgg cgtggccgcg gccggccacc acgagccgcc cttcgtcttg | 1020 |
| ggcaacaacg ggggcgcggc cgcctttgaa gggacgacaa gacagcaggg ctccggcgct | 1080 |
| cactttgaag ctgccgcggc gccgccgccg ccagcgttca tagatttcct cggggtcgga | 1140 |
| gccacatga | 1149 |

<210> SEQ ID NO 8
<211> LENGTH: 6180
<212> TYPE: DNA
<213> ORGANISM: Zea mays

<400> SEQUENCE: 8

| | |
|---|---|
| ttgttttacc taaggtttct tcatttctct gttttcccgt atgtgtaggg ccttcccctc | 60 |
| cctcccctca cctcccccgg cggcggcgcc cctcacccct cctttttcc ccaccggtgc | 120 |
| gaccccctct ccccccggca gtcagcggcg gcggcggagg cgcccgcgcc cagcccgcag | 180 |
| ccctgcacgc gcgctcctat gcccctgcct gcgcgcccccc ccctgcgc agccccctcc | 240 |
| ccctcctcct ctctcttcta tggatgggag gaagaagatg agatgagtag aaagatggcg | 300 |
| gttttgtaat ttagtacgca tgaatttcag tttagtttaa aacagtgata gcttttacgt | 360 |
| tttaaacccg atttaatcct tttaagttgt gttagattta tattcaaatt atctacatgt | 420 |
| tagaagtatt ttccctaata ttgtatattt tatttaattt atttaaacat tgtttgatc | 480 |
| gatgactaat agaacgacgt tttatttaaa tctaatttat aatttcgaat tgcacatttg | 540 |
| taaatcaaca tcagcgcagt caatgttaac tgaactattc tattaaataa ttagttagtt | 600 |
| taatcatatt atttgtttat tagtgttcgc gtatggtgtt ggcctgcgcg ccgtgcgcgt | 660 |
| accgtgcgcg tgcggccgta ctatttcacg ctttacgtat tacgtcttac accactaatt | 720 |
| cgtcttgctt agagtcgcta atgttattta aagtaattat ttaactaaga gttgttagtg | 780 |
| caatacaact aattaaaact aggcgatagc tctagttgca tttaacaaat agcgattaat | 840 |
| atagttacgt cgaattaaat attctaatta atacttactt agtgtaaaca cgttaacccc | 900 |
| tcgaccgtag cttcgactat tgcggttctt tttctcgcgt aaccgtagaa gtgctctcta | 960 |
| ttttatattg ctcgctttta taatattata tattgtatgg tgtaatgttc ttatgcaaat | 1020 |
| atattattgg gggccttccc cttccgaagg tcctaaaaac ataattaacc atttggcttt | 1080 |
| agcatgaact attacaggaa gcttcgtctc taggagataa gcctctttct aatgacgaaa | 1140 |
| gacacacatg atgaagatag atctaaagaa gacaagagta aacgccgaag ctaatagcgg | 1200 |
| acataaatag ctgaagaagg aaaacggagg aatgctgata atggctgaag aaggaaaaga | 1260 |
| ctatttggtc ctttataatt tgtattacga tcatgtgtaa acattaagaa cataaatgaa | 1320 |
| cttttgctcg ggctgcgtcc cgtgcctata aatagatgaa cagtaacatc gtactgttca | 1380 |
| ggctgaattg tattcactct ctcgcatcct cgccttcaac aagccgaagg tactaatgta | 1440 |
| atattattat tatagatatt catatatgtt ttatggaatg aaagaataaa agaattatta | 1500 |
| tgatttaact atcatattta tttccttgta tccctatctt tgtattgata tgatgaaggt | 1560 |
| gtgtccttcc tgaccttcgt ccgaagagta ttacacccgt aaggagataa tacttcgagg | 1620 |
| gacgaaggtc ctttacgatt aacaattgtg ttgccttgtt cttgacttac accatttgag | 1680 |
| aacaagtgac caacatttgg cgcccacctc cggtgaactc acttccacaa ccttcggcaa | 1740 |
| gcatcaacct tcgacatgcc gccgaagaag gcaacgatgc cagccactgg acacaaacca | 1800 |

```
ggacgcactc tccttgcgcg aggctaggaa ccaaaagagg aaggccacta gcccaactct    1860 tcaaaggac  cagcttgacc aggagatcag ggatttagaa gcaatccatc aacaggtgca    1920
aagaaaaagt gagaaaatgc tccggctggc cgatcttcag aagaagattg acgacgcagc    1980
tgaggagatg cgtcatctta ctcaagatgg ccaagatcga aggcctcagc acagggagct    2040
tcgtcaggag agctcattca acgaagatga atggtacaat gactttcatc atggtaactt    2100
tacttttgat gatgcttctc ctctggtggc agaattgcag gctacccgt ggccataatc     2160 ttacaagcca ccttagttgc ccatgtatga tgggcactcg gatccaaagc aatttctgat    2220
gagttacgag gcaacaatat cctcgtacgg gggcaacgct actatcatgg caaagttctt    2280
cgtcatggca gtcagaagcg tggcctagac atggtattcc tcccttagat cagggacaat    2340
cacatcatgg cagaagctga aggatatgct ggtcactagt ttccagggct ttcagacaaa    2400
gccaattatt gctcaggcct tgttccagtg cacgcaagac caggaggagt acctgtaggc    2460
ttacgtccga aggttcctac gtttgagagc tcaatcgcct atagtgccca atgaaattgt    2520
cattgaggcc atgattaagg ggcttcggcc aggacctaca accaaatatt cgctaggaa     2580 gcccccacaa accctggaga agttccttaa gaagatggat gagtacatct gggtcgataa    2640
tgatttccgc caaagaaggg aggaagcata caagttttct gagatgacca ggggcttcgg    2700
aggaggactt catcccaggc atatcaggtc aatccataac tccaatgcta acgatgaaag    2760
gcccaatagt gctcagagcg ccatcatcg  ctcacagtct tcgagcatgc agcaaacttc    2820
ctataggcca ccagctccga gaggcagagg aggaagaagc ttcagtggag gaagattcgg    2880
taatcaaccc aggaagttgt attgcctctt ctgtgacgag gttaagggcc acacaacaag    2940
gacgtgtcag gtcacaatcc agaagcaaaa ggaaattgtt gaagccgagg catggcagaa    3000
ccagccgaag caagtccttt atactgcttc gtgctactct ccatacatcc agaatatgt     3060 aggcaaccaa tagactacag cttcaccaag tcactcccaa gcttcctggg cccaattact    3120
gccaccccca ccaatggtgc ctgccccaag ccatgataag cagccagaag ggcacctttg    3180
gcctcaacaa caacgtgatc ttcgggatca gtctgaggtt cgcacagtta acagtactgt    3240
acctgaggcc aggcacatct actgaagatg acacatcgtt ttggtcaaaa gaaagtcctg    3300
atatgtccca tttctactat ttttttgcttt catatttctg ttgcaaaaga caatatagta    3360
aggtttaaca ttcaacttga tgtaataaac ctatcgttac accatcgagt gtgacaaaat    3420
caagttccta agctccaaag acgttcctaa gggagcgcag agtaagttct gaagctcaaa    3480
agtcgtttct aagggaatac agagccaaaa tgccacctaa gtaaaaggtg aagagactcc    3540
aaatcactcc taagggaatg cagagcctga atgccaccta agtaacaggt gaagaagttc    3600
aaaagtcgtt cctaagggga tgcagagctg aaatactacc taagtaaagg gtgaagagac    3660
tccaaagtcg ttcctaaggg gacgcaaagt ctggatgtgt attcgtgtag gttttttta    3720 ccttcggcat aaatattatt ttgcatcata ccatcataac atatcgcata gcattgtatc    3780
atacatcatt ttgcatcagc aaaaggctat ggagaagaag ggaaattgct ccttcgcaac    3840
atgtatcttc ggtggatata atttactaca cgaagcccac cttcgtcaac atctttgagc    3900
aaactcaatg ttttatactc gaacaaaata tattgagata gattttccat tcttcgtggg    3960
aacgccaagc tgattcgagg tgtttagata tttgatttat tagttctgcg gagcacaaaa    4020
ggcttttgcc tacatggtag tagatgatgt tatttatgaa cagcagccct caactcaagt    4080
gatgcattat gatattatta ttattattat cgggagtttt ggagacacaa taatgtcgct    4140
```

-continued

```
gggtgtggac gaacgaagcc gtgcgtgcgt cgtgcgccg ggggcagagc ggcagcggca    4200
cagtgcgcgg ggcctgcgcc ccccgtgca gttgaaaaga taggtgcctg tagtggttgc    4260
agggctcatt cagacagcac tggagggcat gcatgttctg tcaaggcatc agggctccgc    4320
gcctgggaga tagatcatct catctactct actactagtc tactacccag caactcaaa    4380
gcaatgcaag agagcctgtt tattgttggg actcgtaccc cgcccagcag ctctgcacat    4440
ttaacaatcc cactcatgct tttgtttctt attattatta ttattattac aaaaaaaaa    4500
gaaaataggc cgaacctgct gcctgaaacc cgcatgcacc acctgcaggg gcctctatt    4560
aatttgcgct ggtctcgtac ttgacgttgc gtcctgctgc tcctttgaga ttcctgctgg    4620
aagattgcga tctctgcctt cttttctttt cttctttttt tttaaaaaaa acaaaaggca    4680
tcagtttgag tacttttatt ggctaagtac gaaaacatta actcccggtc aagagaaagg    4740
tggtgtgtgt ttgtgcgtgc gtgcgtgtgt gtttaataag gcccagcagc ctccctgagc    4800
tggtcgtttt atatggccag tcaagcgttg cagagtagta tattgtctat gcattactac    4860
ttgactaagc agccactgaa ctctgcacag gtctacttgg ccctcagagt acacattatt    4920
caccggccag tcgtcgtgca aagagcacag tttctgttac cgctgatgat tggatgccgt    4980
aattaatagc cggttcccat tcccgtccag atttccatcg cgattcgcga ggaaaagcgt    5040
ccgtgtgtgt gtacacgcgc ttcaaactgt tgggcgcatg tacacgtacg tacgctcgga    5100
cgtaccgatc cactgttgag agtgaaaact gaatggggag ggggagagag agaagaaaga    5160
gaaagagacc agtagcaagt agtagtagat cgacgatcag gcaggcgggc tacagtgcta    5220
accttctctc tctctatctc tctctggccg tgcgtcgtcc ttgcaagcca cacatgtggt    5280
gagatgacat ctacacgtgc ggtggggacg cccgatgctt tgttaaactc ggtgaaagcc    5340
atgagagatg cagcgggcg gtgtggtggt agtagtagac agctgggaca gtgacaagcc    5400
ttgcgtgcag taagatcttc tgcgcccttaa ccttaattac ccctcctccg cctccagttt    5460
ttaccgcgcg aacccctagta aaataactcc cgccagtgtg ctctctctct ctctctacga    5520
ctatttttca ccccttcttt cccagttccg tgccttgcac ttcgcctttt caaaaagctt    5580
ttgccatatg cagtacacat gtgttaatag agtagtaact ttcttttctt ttgcaaactg    5640
attgagatcc aaagcaagca agcaagcaag ctgtatgtac ttgcaaacaa caccccttggt    5700
agctatcccc ctcccgtgcc cgtgcccgtg ccgtgccct gcaatccccg acccggagca    5760
gcagccacca ccggcgcggc gtcccgcgag ccagcacaga cgatccctcc ccattcccgc    5820
ccgcactgcc cagcaccagg aggagcagct agcctatcca acagtgaaaa gcacacacgc    5880
gttccggact ccggactacg cccggccctc ccctcccctc ccctcctcc tgcggttttt    5940
agacagggga gtgcgtgcgc ccgagcgatc cgtccatctg acgggaatga gagggtgcgt    6000
gcgtgcgtgg gggagagtga gatgcctgcc tccctgtagc gtgtaggagt agctctggcc    6060
tcttcctcta cctccagccg tgcggttttc tgctgcggaa gaaacgggag cagtgtcgct    6120
cgtcccgctc gcgcgcacat cctcaactcg tctccgtctc tcccgcggca actgacgacg    6180
```

<210> SEQ ID NO 9
<211> LENGTH: 382
<212> TYPE: PRT
<213> ORGANISM: Zea mays

<400> SEQUENCE: 9

Met Pro Cys Ser Ser Pro Ala Pro Thr Trp Leu Leu Arg Val Ser Pro
1               5                   10                  15

```
Ala Ala Ala Ala Ala Asp Gln Ala Ala Ala Ser Ser Ser Cys Ser Ser
             20                  25                  30

Lys Gly Gly Gly Arg Val Leu Thr Ala Gly Thr Thr Thr Met Asp Thr
         35                  40                  45

Ala Ala Thr Ala Ala Ala Gly Gly Asn Ala Ala Asp Leu Gln Glu Ser
     50                  55                  60

Ser Ser Ser Gly Gln Ser Arg Leu Ala Ala Arg Gly His Trp Arg Pro
65                  70                  75                  80

Ala Glu Asp Ala Lys Leu Arg Glu Leu Val Ala Leu Tyr Gly Pro Gln
             85                  90                  95

Asn Trp Asn Leu Ile Ala Glu Lys Leu Asp Gly Arg Ser Gly Lys Ser
             100                 105                 110

Cys Arg Leu Arg Trp Phe Asn Gln Leu Asp Pro Arg Ile Ser Lys Arg
             115                 120                 125

Pro Phe Ser Asp Glu Glu Glu Arg Leu Met Ala Ala His Arg Phe
             130                 135                 140

Tyr Gly Asn Lys Trp Ala Met Ile Ala Arg Leu Phe Pro Gly Arg Thr
145                 150                 155                 160

Asp Asn Ala Val Lys Asn His Trp His Val Ile Met Ala Arg Lys Tyr
             165                 170                 175

Arg Glu Gln Ser Thr Ala Tyr Arg Arg Arg Lys Leu Asn Gln Ala Val
             180                 185                 190

Gln Arg Lys Leu Glu Ala Ala Ser Ala Ala Val Ala Met Pro Pro Gly
             195                 200                 205

Ala Gly Ala Gly Asp Val Ala Val Gly Gln His His His Leu Leu Ala
             210                 215                 220

Ala Ala Ala Ala Ala His Ala His Asp Ala Ala Tyr Ser Phe Ala Ala
225                 230                 235                 240

Asp Pro Tyr Gly Phe Gly Ile Arg His Gln Tyr Cys Thr Phe Pro Phe
             245                 250                 255

Pro Pro Gly Ala Ala Ser Ala Glu Asp Pro Pro Pro Thr Gln Ile
             260                 265                 270

His Pro Phe Cys Leu Phe Pro Gly Pro Ser Ser Ala Ala Ala His Ala
             275                 280                 285

Asp Ser Arg Arg Leu Pro Trp Pro Pro Ser Ser Asp Ala Pro Gly Val
             290                 295                 300

Ala Arg Tyr Gly Glu Pro His Gln Leu Leu Gln Leu Pro Val Gln Ser
305                 310                 315                 320

Gly Trp Ile Asp Gly Val Gly Val Ala Ala Gly His His Glu Pro
             325                 330                 335

Pro Phe Val Leu Gly Asn Asn Gly Gly Ala Ala Ala Phe Glu Gly Thr
             340                 345                 350

Thr Arg Gln Gln Gly Ser Gly Ala His Phe Glu Ala Ala Ala Ala Pro
             355                 360                 365

Pro Pro Pro Ala Phe Ile Asp Phe Leu Gly Val Gly Ala Thr
             370                 375                 380
```